US010259922B2

(12) United States Patent
Zare et al.

(10) Patent No.: US 10,259,922 B2
(45) Date of Patent: Apr. 16, 2019

(54) METHODS FOR MODIFYING A HYDROPHOBIC POLYMER SURFACE AND DEVICES THEREOF

(71) Applicant: The Board of Trustees of the Leland Stanford Junior University, Stanford, CA (US)

(72) Inventors: Richard N. Zare, Stanford, CA (US); Samuel Kim, Palo Alto, CA (US); Raffick Amid Razzakk Bowen, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 161 days.

(21) Appl. No.: 15/033,844

(22) PCT Filed: Nov. 4, 2014

(86) PCT No.: PCT/US2014/063935
§ 371 (c)(1),
(2) Date: May 2, 2016

(87) PCT Pub. No.: WO2015/069662
PCT Pub. Date: May 14, 2015

(65) Prior Publication Data
US 2016/0251490 A1     Sep. 1, 2016

Related U.S. Application Data

(60) Provisional application No. 61/900,909, filed on Nov. 6, 2013.

(51) Int. Cl.
*C08J 7/12* (2006.01)
*B01L 3/00* (2006.01)
(Continued)

(52) U.S. Cl.
CPC .......... *C08J 7/12* (2013.01); *A61B 5/150343* (2013.01); *A61L 29/06* (2013.01); *A61L 29/14* (2013.01);
(Continued)

(58) Field of Classification Search
CPC .................. C08J 7/12; A61B 5/150343
See application file for complete search history.

(56) References Cited

U.S. PATENT DOCUMENTS 4,078,143 A     3/1978  Malik et al.
4,985,026 A *   1/1991  Kasai ................. B01L 3/5082
                                                422/914
(Continued)

FOREIGN PATENT DOCUMENTS

CN     102534843 A  *  7/2012
EP         0033754 A1 *  8/1981  ............... C08J 7/18
(Continued)

OTHER PUBLICATIONS

CN102534843 translation Jul. 4, 2012 (Year: 2012).*
(Continued)

*Primary Examiner* — Cachet I Sellman
(74) *Attorney, Agent, or Firm* — Khin K. Chin; Bozicevic, Field & Francis LLP

(57) ABSTRACT

Aspects of the invention include methods for modifying a surface of a non-porous hydrophobic polymer substrate having a backbone containing electrophilic linkages. In practicing methods according to certain embodiments, a liquid composition having a nucleophilic reagent and a catalyst is contacted with the surface of the non-porous hydrophobic polymer substrate and maintained in contact with the surface of the polymer substrate in a manner sufficient to convert at least a portion of the surface from hydrophobic to hydrophilic while retaining the mechanical
(Continued)

a)

b)

and optical properties of the polymer substrate. Substrates, including containers, having one or more hydrophilic surfaces and kits suitable for practicing the subject methods are also described.

13 Claims, 15 Drawing Sheets

(51) Int. Cl.
*A61L 29/06* (2006.01)
*A61L 29/14* (2006.01)
*A61B 5/15* (2006.01)

(52) U.S. Cl.
CPC ......... *B01L 3/5082* (2013.01); *A61L 2400/10* (2013.01); *A61L 2400/18* (2013.01); *B01L 2300/0832* (2013.01); *B01L 2300/12* (2013.01); *B01L 2300/16* (2013.01); *C08J 2367/02* (2013.01); *C08J 2369/00* (2013.01)

(56) References Cited

U.S. PATENT DOCUMENTS

| | | | |
|---|---|---|---|
| 5,121,636 A | | 6/1992 | Seiter et al. |
| 5,589,563 A | | 12/1996 | Ward et al. |
| 5,668,186 A | | 9/1997 | Brunelle et al. |
| 5,912,275 A | | 6/1999 | Hall et al. |
| 6,077,235 A | * | 6/2000 | Serpentino .......... B01L 3/50825 436/18 |
| 6,132,825 A | * | 10/2000 | Frisk ................. B01J 31/06 428/35.7 |
| 6,632,493 B1 | * | 10/2003 | Hildebrand, IV ... B65D 1/0215 222/206 |
| 7,696,378 B2 | | 4/2010 | Hidaka et al. |
| 9,988,170 B2 | * | 6/2018 | Sato .................. A61L 2/22 |
| 2003/0203991 A1 | | 10/2003 | Schottman et al. |
| 2005/0288508 A1 | | 12/2005 | Hedrick et al. |
| 2006/0286322 A1 | | 12/2006 | Crawford et al. |
| 2008/0124450 A1 | | 5/2008 | Pacetti |
| 2009/0023823 A1 | * | 1/2009 | Kim ................... C08G 18/4018 521/48.5 |
| 2010/0133088 A1 | | 6/2010 | Hajek et al. |
| 2011/0003949 A1 | | 1/2011 | Hedrick et al. |
| 2012/0223270 A1 | | 9/2012 | Alabdulrahman et al. |
| 2012/0302781 A1 | | 11/2012 | Hedrick et al. |
| 2013/0266491 A1 | * | 10/2013 | Murata ................ B01L 3/5027 422/547 |
| 2014/0257450 A1 | * | 9/2014 | Jung .................. A61F 2/06 623/1.1 |
| 2015/0005193 A1 | * | 1/2015 | Phillips .............. C12Q 1/26 506/11 |

FOREIGN PATENT DOCUMENTS

| | | | | |
|---|---|---|---|---|
| EP | 0033754 B1 | | 4/1997 | |
| EP | 1229068 A1 | * | 8/2002 | .............. C08J 7/123 |
| JP | 11302208 A | * | 11/1999 | .............. C08J 11/16 |
| WO | WO 97/20886 A1 | | 6/1997 | |
| WO | WO 97/46590 A1 | | 12/1997 | |
| WO | WO 00/47659 A1 | | 8/2000 | |
| WO | WO 2004/044012 A1 | | 5/2004 | |
| WO | WO 2009/010435 A2 | | 1/2009 | |
| WO | WO 2012/047360 A1 | | 4/2012 | |
| WO | WO-2012057042 A1 | * | 5/2012 | .............. C08J 7/123 |

OTHER PUBLICATIONS

Bowen et al. "Impact of blood collection devices on clinical chemistry assays", Clinical Biochemistry 43, 2010, pp. 4-25.

Campanelli et al. "Kinetics of Glycolysis of Poly(Ethylene Terephthalate) Melts", Journal of Applied Polymer Science, vol. 54, 1994, pp. 1731-1740.

Carta et al. "Chemical Recycling of Poly(ethylene terephthalate) (PET) by Hydrolysis and Glycolysis", Environ Sci & Pollut Res 10 (6), 2003, pp. 390-394.

Chen et al. "Depolymerization of Poly(Ethylene Terephthalate) Resin Under Pressure", Journal of Applied Polymer Science, vol. 42, 1991, pp. 1501-1507.

Choi, H. "Hygroscopic Poly(ethylene terephthalate) by Nonaqueous Alkaline Glycolysis", Ind. Eng. Chem. Res., vol. 46, No. 24, 2007, pp. 7891-7895.

Güçlü et al. "Glycolysis of Poly(ethylene terephthalate) Wastes in Xylene", Journal of Applied Polymer Science, vol. 69, 1998, pp. 2311-2319.

Imran et al. "Metal-Oxide-Doped Silica Nanoparticles for the Catalytic Glycolysis of Polyethylene Terephthalate", Journal of Nanoscience and Nanotechnology, vol. 11, 2011, pp. 824-828.

Kao et al. "Investigation of catalytic glycolysis of polyethylene terephthalate by differential scanning calorimetry", Thermochimica Acta 292, 1997, pp. 95-104.

Kim et al. "Permanent Hydrophilic Surface Formation by Ion Assisted Reaction", Refereed Proceedings, Heat Exchanger Fouling and Cleaning: Fundamentals and Applications, Engineering Conferences International, Art. 15, 2003, pp. 1-8.

Oku et al. "Alkali Decomposition of Poly(ethylene terephthalate) with Sodium Hydroxide in Nonaqueous Ethylene Glycol: A Study on Recycling of Terephthalic Acid and Ethylene Glycol", Journal of Applied Polymer Science, vol. 63, No. 5, Jan. 31, 1997, pp. 595-601.

Pelagade et al. "Investigation of Surface Free Energy for PTFE Polymer by Bipolar Argon Plasma Treatment", Journal of Surface Engineered Materials and Advanced Technology, 2012, 2, pp. 132-136.

Shukla et al. "Depolymerization of Poly(ethylene terephthalate) Waste", Journal of Applied Polymer Science, vol. 85, 2002, pp. 1765-1770.

Shukla et al. "Recycling of waste PET into useful textile auxiliaries", Waste Management 28, 2008, pp. 51-56.

\* cited by examiner a)

b)

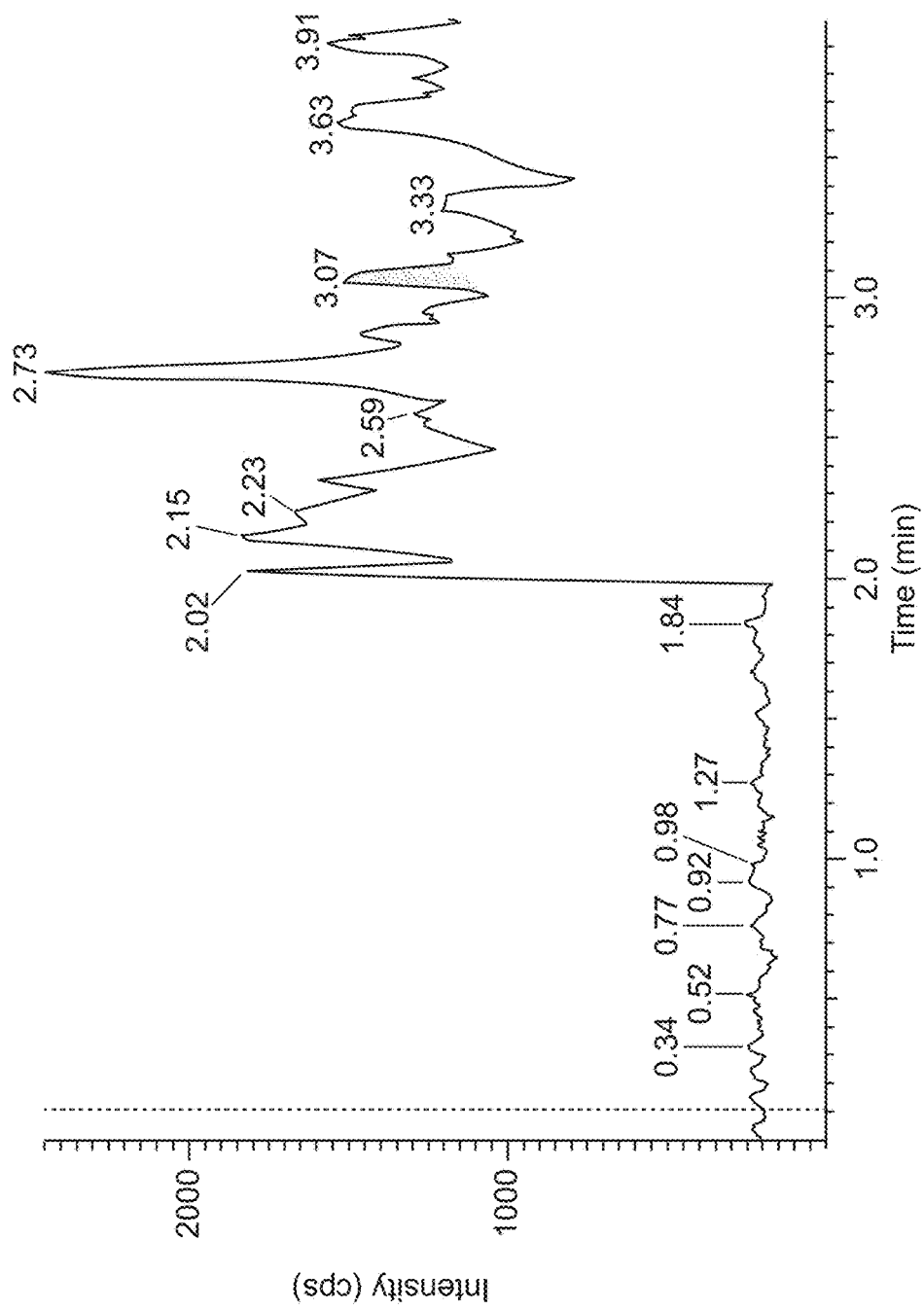

| Analyte | Mean (SD) | | | | | | P |
|---|---|---|---|---|---|---|---|
| | Glass | Modified PET | Vacuette™ | PRT | RST™ | SST™ | |
| Albumin (g/dL) | 4.0 (0.03) | 3.9 (0.00) | 3.9 (0.00) | 4.0 (0.00) | 4.0 (0.00) | 3.9 (0.00) | 0.027 |
| ALP (U/L) | 371 (2.9) | 370 (2.2) | 363 (3.5) | 376 (4.5) | 388 (1.2) | 370 (4.0) | 0.002* |
| ALT (U/L) | 95 (1.2) | 96 (1.2) | 97 (1.9) | 96 (0.3) | 95 (1.2) | 96 (0.6) | 0.697 |
| AST (U/L) | 194 (0.6) | 197 (0.9) | 194 (0.7) | 195 (0.9) | 196 (2.3) | 196 (1.0) | 0.649 |
| Urea Nitrogen (mg/dL) | 50 (0.3) | 50 (0.3) | 49 (0.00) | 49 (0.7) | 50 (0.6) | 50 (0.0) | 0.586 |
| Total Calcium (mg/dL) | 12.0 (0.03) | 12.0 (0.03) | 12.0 (0.03) | 12.0 (0.07) | 12.1 (0.03) | 12.1 (0.03) | 0.047 |
| Chloride (mmol/L) | 101 (0.8) | 100 (0.0) | 101 (0.7) | 100 (0.0) | 100 (0.6) | 99.3 (0.3) | 0.187 |
| Creatinine (mg/dL) | 5.97 (0.00) | 5.93 (0.03) | 5.93 (0.03) | 5.93 (0.03) | 5.90 (0.00) | 5.93 (0.07) | 0.947 |
| Total CO$_2$ (mmol/L) | 30.2 (0.2) | 30.3 (0.4) | 32.3 (0.3) | 29.7 (0.2) | 29.7 (0.2) | 30.9 (0.3) | <0.0001* |
| Glucose (mg/dL) | 285 (1.2) | 284 (2.3) | 283 (0.7) | 285 (2.9) | 286 (0.9) | 287 (0.60) | 0.701 |
| Potassium (mmol/L) | 6.1 (0.03) | 6.2 (0.03) | 6.2 (0.03) | 6.2 (0.03) | 6.2 (0.03) | 6.2 (0.00) | 0.0273 |
| Sodium (mmol/L) | 148 (0.3) | 151 (0.0) | 149 (0.3) | 151.3 (0.3) | 151 (0.3) | 150 (0.6) | 0.001* |
| Total Bilirubin (mg/dL) | 4.97 (0.00) | 5.02 (0.01) | 4.98 (0.01) | 5.00 (0.02) | 5.00 (0.01) | 5.03 (0.01) | 0.021 |
| Total Protein (g/dL) | 7.03 (0.03) | 7.07 (0.03) | 7.03 (0.03) | 7.07 (0.03) | 7.10 (0.00) | 7.10 (0.00) | 0.278 |

Figure 10

| Analyte | Mean (SD) | | | | | | P |
|---|---|---|---|---|---|---|---|
| | Glass | Modified PET | Vacuette™ | PRT | RST™ | SST™ | |
| Albumin (g/dL) | 4.3 (0.08) | 4.4 (0.12) | 4.4 (0.10) | 4.3 (0.10) | 4.3 (0.10) | 4.3 (0.10) | 0.985 |
| ALP (U/L) | 83 (5.5) | 82 (7.1) | 85 (6.2) | 83 (6.2) | 82 (6.0) | 83 (6.4) | 0.999 |
| ALT (U/L) | 19 (2.1) | 19 (2.0) | 19 (2.1) | 18 (1.9) | 19 (1.6) | 19 (1.5) | 0.999 |
| AST (U/L) | 23 (1.8) | 25 (1.7) | 24 (1.7) | 23 (1.9) | 23 (1.7) | 24 (1.7) | 0.868 |
| Urea Nitrogen (mg/dL) | 14 (1.2) | 14 (1.2) | 14 (1.30) | 14 (1.3) | 14 (1.2) | 14 (1.3) | 0.999 |
| Total Calcium (mg/dL) | 9.3 (0.09) | 9.2 (0.08) | 9.3 (0.08) | 9.3 (0.09) | 9.3 (0.08) | 9.3 (0.09) | 0.973 |
| Chloride (mmol/L) | 103 (0.6) | 103 (0.7) | 103 (0.7) | 103 (0.5) | 103 (0.6) | 103 (0.7) | 0.999 |
| Creatinine (mg/dL) | 0.88 (0.05) | 0.84 (0.05) | 0.88 (0.05) | 0.89 (0.05) | 0.91 (0.06) | 0.91 (0.05) | 0.981 |
| Total CO₂ (mmol/L) | 22.1 (0.7) | 19.9 (0.6) | 20.6 (0.6) | 21.3 (0.6) | 21.0 (0.6) | 20.3 (0.6) | <0.010 |
| Glucose (mg/dL) | 115 (14.4) | 101 (7.5) | 116 (14.1) | 115 (14.7) | 117 (14.4) | 115 (14.4) | 0.987 |
| Potassium (mmol/L) | 3.9 (0.01) | 3.7 (0.01) | 3.9 (0.01) | 4.0 (0.08) | 4.0 (0.10) | 4.0 (0.01) | 0.602 |
| Sodium (mmol/L) | 142 (0.4) | 142 (0.5) | 142 (0.4) | 142 (0.3) | 142 (0.3) | 142 (0.4) | 0.969 |
| Total Bilirubin (mg/dL) | 0.40 (0.05) | 0.40 (0.06) | 0.39 (0.05) | 0.36 (0.05) | 0.40 (0.05) | 0.40 (0.05) | 0.999 |
| Total Protein (g/dL) | 7.56 (0.12) | 7.80 (0.14) | 7.59 (0.12) | 7.49 (0.11) | 7.58 (0.11) | 7.55 (0.11) | 0.732 |

METHODS FOR MODIFYING A HYDROPHOBIC POLYMER SURFACE AND DEVICES THEREOF

INTRODUCTION

Blood collection and processing are two major steps in pre-analytical laboratory testing. The proper blood collection and timely processing, by well-trained staff using appropriate devices, are needed to ensure test reliability. Plastic blood collection devices are widely regarded as inert specimen carriers. However, some studies show statistically and clinically significant differences in certain clinical chemistry test results from plastic blood collected in different types of serum evacuated blood collection containers. Surfactants and other components used to modify the properties of plastic blood collection containers can be leached from the walls and can often interfere with clinical chemistry test results. This can sometimes cause inaccurate and irreproducible clinical chemistry results forcing a laboratory to perform costly retesting and/or recollection. Glass containers can be suitable surface for many medical applications, but are generally avoided because of safety concerns about fragility and the dangers associated with sharp glass from broken containers. In general, the surface characteristics of most polymers are hydrophobic. Such hydrophobic characteristic of polymer surface gives many limitations. Hydrophobic polymer surfaces can give rise to severe problems in applications which require a wettable surface.

There is therefore a need to develop containers which exhibit bias-free performance, having desirable properties which do not interfere with the contents within the container, but still meet current safety standards.

SUMMARY

Aspects of the invention include methods for modifying a surface of a non-porous hydrophobic polymer substrate having a backbone containing electrophilic linkages. In practicing methods according to certain embodiments, a liquid composition having a nucleophilic reagent and a catalyst is contacted with the surface of the non-porous hydrophobic polymer substrate and maintained in contact with the surface of the polymer substrate in a manner sufficient to convert at least a portion of the surface from hydrophobic to hydrophilic while retaining the mechanical and optical properties of the polymer substrate. Embodiments of the present disclosure have no leachable residue on the produced hydrophilic surface when exposed to water. Substrates, including containers, having one or more hydrophilic surfaces and kits suitable for practicing the subject methods are also described.

BRIEF DESCRIPTION OF THE FIGURES

FIGS. 3a-c depict de-convoluted chromatograms from LC-MS analyses of calibrator samples in a glass test tube, an unmodified polyethylene terephthalate test employing surface adhered surfactants and a polyester test tube modified according to the subject methods in certain embodiments.

FIG. 4a shows FT-IR spectra of unmodified PET (black) and modified PET (red) obtained using an ATR mode. FIG. 4b difference spectra obtained by subtracting transmittance values of unmodified PET from those of modified PET. Prominent vibrational frequencies and their corresponding chemical bond types are noted.

FIG. 5a shows FT-IR spectra of unmodified PET (Unmod n=1-3) and modified PET (Mod n=1-3) obtained using an attenuated total reflection (ATR) mode. FIG. 5b shows difference spectra obtained by subtracting average transmittance values of unmodified PET from those of modified PET.

FIGS. 6a-c show how contact angle measurements are made using the sessile drop method (left column) and the captive bubble method (right column): FIG. 6a depicts schematics of the two contact angle measurement modes; FIG. 6b shows results for polyethylene terephthalate and FIG. 6c shows results for polycarbonate, and their chemical modifications using EG.

FIG. 7 shows contact angle measurements for polystyrene surfaces, unmodified and modified according to the subject methods with ethylene glycol and with glycerol.

FIG. 8a shows unmodified PET. FIG. 8b shows PET modified according methods of the present disclosure according to certain embodiments. Serum tubes containing human blood are shown before centrifugation in FIG. 8c and after centrifugation in FIG. 8d. The five tube types shown include: Glass (I), Greiner (II), modified PET (III), RST (IV), and SST (V).

FIG. 9a shows tubes modified with ethylene glycol in the presence of 1,5,7-triazabicyclo[4.4.0]dec-5-ene at 22° C. FIG. 9b shows tubes modified with ethylene glycol in the presence of 1,5,7-triazabicyclo[4.4.0]dec-5-ene at 55° C. FIG. 9c shows a comparison of tubes modified with ethylene glycol in the presence of potassium hydroxide.

FIG. 10 depicts a summary of clinical chemistry tests conducted on quality control materials in glass, Greiner, Vacuette, PRT, RST, SST and test tubes modified according to methods of the present disclosure according to certain embodiments.

FIG. 11 depicts a summary of clinical chemistry tests conducted on blood samples from healthy volunteers in glass, Greiner, Vacuette, PRT, RST, SST and test tubes modified according to methods of the present disclosure according to certain embodiments.

DEFINITION OF SELECT CHEMICAL TERMINOLOGY

Figure 1:
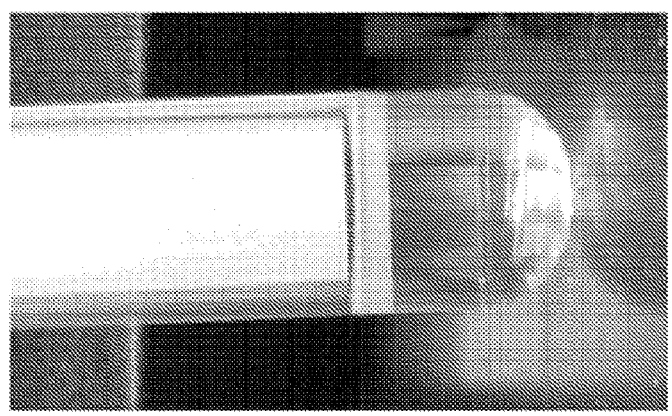
FIGS. 1a-b show an example of visual comparison of water placed in an unmodified polyester test tube and a polyester test tube modified according to the subject methods in certain embodiments.
Figure 1:
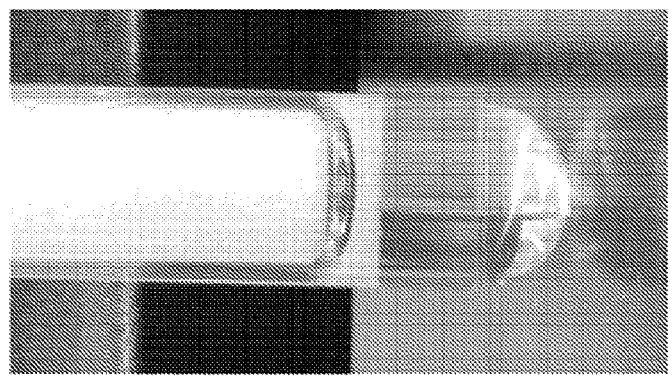

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like. "Alkoxycarbonyl" by itself or as part of another substituent refers to a radical —$C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, $(C_5-C_{14})$ arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a $(C_5-C_{14})$ aromatic. In certain embodiments, each aromatic ring system of an arylaryl group is independently a $(C_5-C_{10})$ aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is $(C_3-C_{10})$ cycloalkyl. In certain embodiments, the cycloalkyl group is $(C_3-C_7)$ cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc.

Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)N R$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O) OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

Aspects of the invention include methods for modifying a surface of a non-porous hydrophobic polymer substrate having a backbone containing electrophilic linkages. In practicing methods according to certain embodiments, a liquid composition having a nucleophilic reagent and a catalyst is contacted with the surface of the non-porous hydrophobic polymer substrate and maintained in contact with the surface of the polymer substrate in a manner sufficient to convert at least a portion of the surface from hydrophobic to hydrophilic while retaining the mechanical and optical properties of the polymer substrate. Substrates, including containers, having one or more hydrophilic surfaces and kits suitable for practicing the subject methods are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present invention provides methods for modifying the surface of a non-porous hydrophobic polymer substrate having a backbone containing electrophilic linkages. In further describing embodiments of the disclosure, methods for modifying the surface of a non-porous hydrophobic polymer substrate having a backbone containing electrophilic linkages are first described in greater detail. Next, surface-modified polymer substrates, including polyester containers, having one or more hydrophilic surfaces prepared by the subject methods are described. Kits suitable for practicing the subject methods are also described.

Methods for Modifying a Surface of a Hydrophobic Polymer Substrate

As summarized above, aspects of the disclosure include methods for modifying a surface of a non-porous hydrophobic polymer substrate having a backbone containing electrophilic linkages. In practicing methods according to certain embodiments, a reagent composition having a nucleophilic reagent and a catalyst is contacted with the surface of the non-porous hydrophobic polymer substrate having a backbone containing electrophilic linkages and maintained in contact with the surface of the polymer substrate in a manner sufficient to convert at least a portion of the surface from hydrophobic to hydrophilic (such as by transesterification) while retaining the mechanical and optical properties of the polymer substrate.

In embodiments of the present invention, the reagent composition is maintained in contact with the non-porous hydrophobic polymer substrate in a manner such that only the surface of the polymer substrate reacts with the reagent composition. By "only the surface" is meant that in practicing the subject methods, only electrophilic linkages positioned at or near the surface of the polymer substrate chemically react with the nucleophilic reagent. Modification of the surface of the polymer substrate with the reagent composition according to embodiments of the invention is a chemical reaction that changes the chemical structure of electrophilic linkages at the surface of the hydrophobic polymer substrate. In some embodiments, reaction of the polymer substrate with the reagent composition results in transesterification of surface electrophilic linkages, such as in a glycolysis reaction of polymer residues at the surface of a polymer container.

In practicing the subject methods the overall structure of the polymer substrate is unaffected (as described in greater detail below) by the nucleophilic reagent apart from reaction (e.g., transesterification) with electrophilic linkages at or near the substrate surface. Depending on the thickness of the polymer substrate, type of polymer, and conditions of the reaction (as described in greater detail below), the depth of surface modification may vary, such as 100 µm or less, such as 50 µm or less, such as 25 µm or less, such as 10 µm or less, such as 1 µm or less, such as 0.1 µm or less and including 0.01 µm or less.

In embodiments, the thickness of surface modification (i.e., hydrophilic surface) is substantially uniform over the entire area of the non-porous polymer substrate surface contacted with the reagent composition. By uniform is meant that the thickness of the surface modification at any given place deviates from the average thickness of the surface modification by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including by 0.1% or less. In certain embodiments, the thickness of the surface modification (i.e., hydrophilic surface) is substantially the same over the entire modified surface area of the non-porous polymer substrate.

As only the surface of the polymer substrate is modified, polymer substrates show little to no depolymerization, degradation or reduction in performance after surface modification in accordance with methods of the invention. In some instances, the subject polymer substrates degrade by 5% or less as a result of surface modification according to the subject methods, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including degrading by 0.1% or less as a result of surface modification according to the subject methods. In certain embodiments, there is entirely no degradation of the polymer substrate. Likewise, methods of the present invention result in little to no depolymerization of the subject polymer substrates. In some instances, the subject methods result in depolymerization of 5% or less of the polymer substrate, such as 4% or less, such as 3.5% or less, such as 3% or less, such as 2.5% or less, such as 2% or less, such as 1.5% or less, such as 1% or less, such as 0.5% or less and including depolymerization of 0.1% or less of the polymer substrate. In certain embodiments, there is entirely no depolymerization of the polymer substrate.

Polymer substrates also show little to no reduction in performance after surface modification in accordance with methods of the invention. By "little to no reduction in performance" is meant that subject methods result in negligible, if any, negative changes in the ability of the polymer substrate to function in a desired manner as compared to the polymer substrate before treatment by the subject methods. For example, where the polymer substrate is a container, the subject methods may result in negligible, if any, negative changes in the ability of the container to hold a volume of liquid, retain a positive pressure of gas, retain a vacuum, etc. In another example, where the polymer substrate is a lens, the subject methods result in negligible, if any, negative changes in the ability of the lens to pass, restrict, focus or collimate light (i.e., little to no changes in optical properties). In some embodiments, the performance of the polymer substrate is reduced by 5% or less as a result of surface modification by the subject methods, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including a reduction in performance by 0.1% or. In certain embodiments, the performance of the polymer substrate is entirely unaffected. In one example, where the polymer substrate is an evacuated test tube, modifying the interior surface of the evacuated test by the subject methods reduces the the ability of the evacuated test tube to retain a vacuum by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including reducing the the ability of the evacuated test tube to retain a vacuum by 0.1% or less as compared to the evacuated test tube before treatment by the subject methods. In certain instances, modifying the interior surface of the evacuated test in accordance with the subject methods has entirely no negative effect on the ability of the evacuated test tube to retain a vacuum.

In embodiments, methods of the invention also result in negligible, if any, change in the thickness of the non-porous polymer substrate. By change in thickness is meant either an increase or decrease in the thickness of the non-porous polymer substrate, in particular at the portions of the polymer substrate contacted with the reagent composition. As such, in these embodiments the thickness of the polymer substrate treated by the subject methods increase or decrease by 1% or less, such as by 0.9% or less, such as by 0.5% or less, such as by 0.25% or less, such as by 0.1% or less, such as by 0.05% or less, such as by 0.025% or less and including by 0.01% or less. In certain embodiments, the thickness of the polymer substrate treated by the subject methods shows no detectable change.

In certain embodiments, where the polymer substrate is the surface of a container, methods of the invention result in negligible, if any, change in the volume of the container. By change in volume is meant either an increase or decrease in volume. As such, in these embodiments the volume of containers treated by the subject methods increase or decrease by 1% or less, such as by 0.9% or less, such as by 0.5% or less, such as by 0.25% or less, such as by 0.1% or less, such as by 0.05% or less, such as by 0.025% or less and including by 0.01% or less. In certain embodiments, containers treated by the subject methods show no detectable change in volume.

In certain other embodiments, methods of the invention also result in negligible, if any, change in the weight of the non-porous polymer substrate. By change in weight is meant either an increase or decrease in the overall weight of the non-porous polymer substrate, in particular at the portions of the polymer substrate contacted with the reagent composition. As such, in these embodiments the weight of the polymer substrate treated by the subject methods increase or decrease by 1% or less, such as by 0.9% or less, such as by 0.5% or less, such as by 0.25% or less, such as by 0.1% or less, such as by 0.05% or less, such as by 0.025% or less and including by 0.01% or less. For example, the weight of the non-porous polymer substrate, in these embodiments, changes by 1 g or less, such as by 0.9 g or less, such as by 0.8 g or less, such as by 0.7 g or less, such as by 0.6 g or less, such as by 0.5 g or less, such as by 0.4 g or less, such as by 0.25 g or less, such as by 0.1 g or less, such as by 0.05 g or less, such as by 0.01 g or less, such as by 0.001 g or less, such as by 1 mg or less, such as by 0.5 mg or less, such as by 0.1 mg or less, such as by 0.05 mg or less, such as by 0.01 mg or less and including changing by 0.001 mg or less. In certain embodiments, the weight of the non-porous polymer substrate treated by the subject methods shows no detectable change.

As described above, aspects include contacting the surface of a solid non-porous hydrophobic polymer substrate with a reagent composition and maintaining the reagent composition in contact with the surface of the polymer substrate in a manner sufficient to convert at least a portion of the surface from hydrophobic to hydrophilic. The term "hydrophilic" is used in its conventional sense to mean having a positive thermodynamic affinity for interaction with polar solvents, including water, where a hydrophilic polymer substrate surface is wettable by water (e.g., water forms a film rather than an aggregated bead). In embodiments of the invention, converting the surface from hydrophobic to hydrophilic includes both reducing the hydrophobicity of the polymer substrate surface and increasing the hydrophilicity of the polymer substrate surface. In some embodiments, converting the polymer substrate surface from hydrophobic to hydrophilic is characterized by a decrease in the contact angle made by water with the surface of the polymer substrate. The term "contact angle" is used in its conventional sense to refer to the angle made by the line at the gas/liquid interface of a droplet of water with the surface of the polymer substrate. In some embodiments, the subject methods decrease the contact angle made by water with the surface of the polymer substrate by 5° or more, such as by 10° or more, such as by 15° or more, such as by 25° or more, such as by 30° or more, such as by 45° or more and including decreasing the contact angle made by water with the surface of the polymer substrate by 60° or more. For example, the decrease in the contact angle made by water may range, such as from about 5° to 90°, such as from about 10° to 80°, such as from about 15° to 75°, such as from about 20° to 70°, such as from about 25° to 65° and including from about 30° to 60°. In certain embodiments, modification of the polymer substrate surface is characterized by converting the surface of a polymer substrate having a contact angle made by water of 90° or greater to a polymer substrate having a surface contact angle made by water of less than 90°. For example, methods may include converting the surface of a polymer substrate having a contact angle ranging from 100° to 180° to a polymer substrate having a surface contact angle ranging from 10° to 80°, such as converting the surface of a polymer substrate having a contact angle ranging from 120° to 160° a polymer substrate having a surface contact angle ranging from 30° to 60° and including converting the surface of a polymer substrate having a contact angle ranging from 130° to 170° a polymer substrate having a surface contact angle ranging from 45° to 75°.

In certain embodiments, methods include maintaining the reagent composition in contact with the non-porous hydrophobic polymer substrate surface in a manner sufficient to produce a surface which makes a contact angle with water that is substantially the same as a glass (borosilicate) surface.

In certain embodiments, methods may also include determining the contact angle made by water with the surface of the polymer substrate. The contact angle may be determined using any convenient protocol, such as for example with a contact angle goniometer. The contact angle made by water with the surface of the polymer substrate may be determined at any time during the subject methods. In some embodiments, the contact angle made by water with the surface of the polymer substrate is determined at regular intervals during methods of the invention, e.g., collecting data every 5 minutes, every 10 minutes, every 15 minutes, every 20 minutes, including every 30 minutes, or some other interval. The contact angle of water with the surface of the polymer substrate may be determined one or more times at any given measurement period, such as 2 or more times, such as 3 or more times, including 5 or more times at each measurement period. In certain embodiments, the number of times the contact angle of water with the surface of the polymer substrate is determined at any given measurement period ranges such as from 2 times to 10 times, such as from 3 times to 9 times, such as from 4 times to 8 times and including from 5 times to 7 times.

In some instances, the contact angle made by water with the surface of the polymer substrate is determined before contacting the reagent composition with the polymer substrate, such as for example, to determine the contact angle made by water with the hydrophobic surface of the polymer substrate. In other instances, the contact angle made by water with the surface of the polymer substrate is determined before contacting the polymer substrate with the reagent composition and after the reagent composition has been removed from contact with the polymer substrate, such as for example to determine the change in the contact angle made by water with the surface of the polymer substrate as a result of surface modification by the subject methods.

In some embodiments, converting the polymer substrate surface from hydrophobic to hydrophilic is characterized by an increase in the surface energy of the polymer substrate surface. The term "surface energy" is used in its conventional sense to refer to the quantification of the free energy of the polymeric monomers at the substrate surface. In some embodiments, the subject methods increase surface energy of the polymer substrate by 5% or more, such as 10% or more, such as by 25% or more, such as by 50%, such as 75% or more and including by 99% or more. For example, the increase in surface energy may range, such as from about 10% to about 99%, such as from about 15% to about 90%, such as from about 25% to about 75% and including from about 35% to about 50%. In certain embodiments, the subject methods increase the surface energy of the hydrophobic polymer substrate by 1.5-fold or more, such as from 2-fold or more, such as 3-fold or more, such as 4-fold or more and including 5-fold or more. For example, the increase in surface energy may range, such as from about 2-fold to about 5-fold, such as from about 2.5-fold to about 4.5-fold, and including from about 3-fold to about 4-fold.

In certain embodiments, methods may also include determining the surface energy of the polymer substrate. The surface energy may be determined using any convenient protocol, such as for example by the Young wetting technique where the contact angle of a drop of water is determined and the thermodynamic surface energy is calculated in accordance with the Young equation. The surface energy of the polymer substrate may be determined at any time during the subject methods. In some embodiments, the surface energy of the polymer substrate may be determined at regular intervals during methods of the invention, e.g., collecting data every 5 minutes, every 10 minutes, every 15 minutes, every 20 minutes, including every 30 minutes, or some other interval. The surface energy of the polymer substrate may be determined one or more times at any given measurement period, such as 2 or more times, such as 3 or more times, including 5 or more times at each measurement period. In certain embodiments, the number of times the surface energy of the polymer substrate is determined at any given measurement period ranges such as from 2 times to 10 times, such as from 3 times to 9 times, such as from 4 times to 8 times and including from 5 times to 7 times.

In some instances, the surface energy of the polymer substrate is determined before contacting the reagent composition with the polymer substrate, such as for example, to determine the inherent surface energy of the hydrophobic polymer substrate. In other instances, the surface energy of the polymer substrate may be determined before contacting the polymer substrate with the reagent composition and after the reagent composition has been removed from contact with the polymer substrate, such as for example to determine the change in surface energy as a result of surface modification by the subject methods.

Non-porous hydrophobic polymer substrates according to embodiments of the invention include polymers having an electrophilic backbone. The term "electrophilic backbone" is used herein in its conventional sense to refer to polymers having a backbone with contains electrophilic linkages that are reactive with and may be subject to cleavage by a nucleophile. In some embodiments, the polymer may be a polyester, a polycarbonate, a polyurethane, including homopolymeric and multipolymeric forms. In certain embodiments, the polymer substrate is a polycarbonate substrate. In certain other embodiments, the polymer substrate is a polyester substrate. Suitable polyesters may be, for example, aliphatic, semi-aromatic or aromatic and can be homopolymeric or multipolymeric. For example, non-porous hydrophobic polyester substrates of interest may include, but are not limited to, substrates of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly($\varepsilon$-caprolactone) and poly($\beta$-propiolactone); poly(alkylene isophthalates) such as poly(ethylene isophthalate); poly(alkylene 2,6-naphthalenedicarboxylates) such as poly(ethylene 2,6-naphthalenedicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexanedimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide).

In embodiments of the invention, a reagent composition having a nucleophilic reagent and a catalyst are contacted with the surface of the non-porous hydrophobic polymer substrate. The term "non-porous" is used herein in its conventional sense to refer to a polymer substrate which lacks sufficient porosity for the permeation of fluids or gases therethrough or sufficient porosity capable of absorbing liquids or gases. In some embodiments, non-porous polymer substrates of interest are non-fibrous. In other embodiments, non-porous polymer substrates are non-woven. Non-porous substrates are capable of restricting the permeation of a liquid or gas therethrough for an extended period of time as well as restrict the absorption of liquid or gas into the polymer substrate. In certain embodiments, non-porous substrates of interest include polymer substrates having pore sizes of 0.1 µm or smaller, such as 0.05 µm or smaller, such as 0.01 µm or smaller, such as 0.005 µm or smaller, such as 0.001 µm or smaller, such as 0.0005 µm or smaller and including 0.0001 µm or smaller. In certain embodiments, polymer substrates of interest have no pores at all.

In embodiments, polymer substrates show little to no change in pore size after treatment by the subject methods. In other words, non-porous polymer substrates remain non-porous after treatment by the subject methods. For example, the subject methods increase the pore size of the non-porous polymer substrates by 3% or less, such as by 2% or less, such as by 1% or less, such as by 0.5% or less, such as by 0.25% or less, such as by 0.1% or less, such as by 0.05% or less, such as by 0.025% or less, such as by 0.01% or less and including increasing the pore size of the non-porous polymer substrates by 0.001% or less. In certain embodiments, there is no detectable increase in the pore sizes of the non-porous polymer substrates.

Non-porous hydrophobic polymer substrates of the invention may be any type of substrate made of a polymer as described above which has a surface area sufficient for contacting with one or more of the subject reagent compositions. Polymer substrates of interest may take any three dimensional shape, including, but is not limited to, single and multi-layer sheets, cylinders, platonic solids (e.g., cubes, tetrahedrons octahedron, trigonal pyramids, square pyramids, icosahedrons, dodecahedrons), tori, quadric solids (e.g., cones, ellipsoids, spheroids, spheres), strips, helices, among other shapes.

In some embodiments, the non-porous hydrophobic polymer substrate is one or more surfaces of a container. Containers of interest, may include but are not limited to, blood collection tubes, test tubes, centrifuge tubes, culture tubes, microtubes, syringes, fluidic conduits, containers for containing chromatography materials (e.g., container walls of a chromatography column), medical tubing including intravenous drug delivery lines, blood transfusion lines, caps, pipettes, petri dishes, microtiter plates (e.g., 96-well plates), flasks, beakers, straws, catheters, cuvettes, polymeric lenses, jars, cans, cups, bottles, rectilinear polymeric containers (e.g., plastic boxes), food storage containers, polymeric bags such as intravenous drug delivery bags, blood transfusion bags as well as large liquid storage containers such as drums and liquid storage silos, among other types of containers.

Where the subject methods are directed to a container, methods may include modifying an interior surface of the container, an exterior surface of the container or a combination thereof. In certain embodiments, methods include contacting an interior surface of the polymer container with the reagent composition and maintaining the reagent composition in contact with the interior surface in a manner sufficient to convert at least a portion of the interior surface of the container from hydrophobic to hydrophilic. In other embodiments, methods include contacting an exterior surface of the polymer container with the reagent composition and maintaining the reagent composition in contact with the interior surface in a manner sufficient to convert at least a portion of the exterior surface of the container from hydrophobic to hydrophilic. In yet other embodiments methods include contacting both an interior surface and an exterior surface of the polymer container with the reagent composition and maintaining the reagent composition in contact with the interior surface and exterior surface in a manner sufficient to convert at least a portion of the interior surface and the exterior surface of the container from hydrophobic to hydrophilic.

In certain embodiments, containers of interest have a volume which varies greatly, ranging from $10^{-3}$ mL to $10^6$ mL, such as from $10^{-2}$ mL to $10^5$ mL, such as from $10^{-1}$ mL to $10^4$ mL and including a volume which ranges from 1 mL to $10^3$ mL.

In embodiments, reagent compositions include a nucleophilic agent and a catalyst. Nucleophilic agents may include, but are not limited to, straight chain or branched aliphatic multihydric alcohols (i.e., polyols). For example, nucleophilic agents of interest may include, but are not limited to, $C_2$-$C_{12}$ dihydric alcohols (such as ethylene glycol, propylene glycol and butylene glycol) $C_3$-$C_{12}$ trihydric alcohols (such as glycerol) multi-arm polyols including 3-arm, 4-arm, 8-arm and branched ethylene, propylene and butylene glycols. In certain embodiments, the nucleophilic reagent is ethylene glycol. In other embodiments, the nucleophilic reagent is glycerol.

The reagent composition may include one or more types of nucleophilic reagent, depending on the type of polymer substrate and conditions employed during the subject methods (e.g., temperature, duration of treatment). In some embodiments, the reagent composition includes only a single type of nucleophilic reagent. In other embodiments, the reagent composition includes two or more types of nucleophilic reagents, such as three or more types, such as four or more types and including 5 or more types of nucleophilic reagents. In some instances, the number of types of nucleophilic reagents ranges, such as from 1 to 5 types of nucleophilic reagents, such as 2 to 4 types of nucleophilic reagents.

The amount of nucleophilic reagent present in the subject reagent compositions may vary, depending on the specific contacting protocol, type of polymer and type of nucleophilic reagent. In some embodiments, the amount of nucleophilic reagent in the subject reagent compositions is 75% by weight or more, such as 80% by weight or more, such as 85% by weight or more, such as 90% by weight or more, such as 95% by weight or more, such 97% by weight or more, such as 98% by weight or more, such as 99% by weight or more, such as 99.5% by weight or more, such as 99.9% by weight or more and including 99.99% by weight or more.

Reagent compositions also include one or more catalysts. In some embodiments, the catalyst is a base. Base catalysts of interest may include, but are not limited to, hydroxide-containing bases, such as potassium hydroxide, sodium hydroxide, calcium hydroxide, ammonium hydroxide, lithium hydroxide, rubidium hydroxide, cesium hydroxide, strontium hydroxide, barium hydroxide. In certain embodiments, the catalyst is potassium hydroxide.

In other embodiments, catalysts of interest include superbases. The term "superbase" is used herein in its conventional sense to refer to class of compounds having a high basicity (e.g., strong affinity for protons) and may include, but are not limited to organic superbases, organometallic superbases and inorganic superbases. In some instances, superbases of interest include but are not limited to phosphazenes, amidines, guanidines, organolithium superbases, organomagnesium superbases, metal amides such as lithium diisopropylamide, Schlosser base, lithium nitride, as well as metal hydrides such as potassium hydride or sodium hydride.

Catalysts of interest may also include guanidine-containing bases. The term "guanidine-containing" bases is used in its conventional sense to refer to the class of organic bases which include the guanidinyl moiety and its derivatives. In some embodiments, guanidine containing bases include compounds of formula (I):

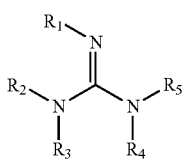

Formula (I)

where:
each of $R^1$, $R^2$, $R^3$, $R^4$ and $R^5$ are independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano.

In some embodiments, each of $R^1$, $R^2$, $R^3$, $R^4$ and $R^5$ are independently selected from hydrogen or substituted or unsubstituted $C_1$-$C_{12}$ alkyl. In certain embodiments, each of $R^1$, $R^2$, $R^3$, $R^4$ and $R^5$ are independently selected from hydrogen, methyl, ethyl, n-propyl, isopropryl, n-butyl and t-butyl.

In certain embodiments, the guanidine-containing compound is 1,1,3,3-tetramethylguanidine. In other embodiments, the guanidine-containing compound is a pentaalkylguanidine compounds of formula (I):

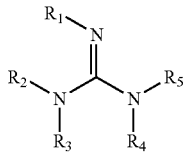

Formula (I)

where each of $R^1$, $R^2$, $R^3$, $R^4$ and $R^5$ are independently a substituted or unsubstituted $C_1$-$C_{12}$ alkyl. In certain embodiments, each of $R^1$, $R^2$, $R^3$, $R^4$ and $R^5$ are independently methyl, ethyl, n-propyl, isopropryl, n-butyl and t-butyl.

In other embodiments, guanidine-containing compounds include cyclic guanidine-containing compounds having a monocyclic ring systems of formula (II):

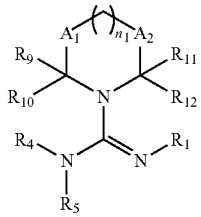

Formula (II)

where $A_1$ and $A_2$ are independently selected from —$NR^6$— and —$C(R^7)(R^8)$—, where $R^6$, $R^7$ and $R^8$ are independently a substituted or unsubstituted $C_1$-$C_{12}$ alkyl; $n_1$ is 0 or 1; and each of $R^9$, $R^{10}$, $R^{11}$ and $R^{12}$ is independently alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

where any two of $R^9$, $R^{10}$, $R^{11}$ and $R^{12}$ together form a five-member or six-member ring.

In certain embodiments, each of $R^6$, $R^7$ and $R^8$ is independently selected from hydrogen, substituted or unsubstituted $C_1$-$C_{12}$ alkyl, substituted or unsubstituted $C_1$-$C_{12}$ cycloalkyl, substituted or unsubstituted $C_1$-$C_{12}$ aryl, substituted or unsubstituted $C_1$-$C_{12}$ alkenyl and substituted or unsubstituted $C_1$-$C_{12}$ alkynyl.

In certain embodiments, each of $R^6$, $R^7$ and $R^8$ is independently selected from hydrogen, methyl, ethyl, n-propyl, isopropryl, n-butyl and t-butyl.

In certain embodiments, each of $R^9$, $R^{10}$, $R^{11}$ and $R^{12}$ is independently selected from hydrogen, substituted or unsubstituted $C_1$-$C_{12}$ alkyl, substituted or unsubstituted $C_1$-$C_{12}$ cycloalkyl, substituted or unsubstituted $C_1$-$C_{12}$ aryl, substituted or unsubstituted $C_1$-$C_{12}$ alkenyl and substituted or unsubstituted $C_1$-$C_{12}$ alkynyl.

In certain embodiments, each of $R^9$, $R^{10}$, $R^{11}$ and $R^{12}$ is independently selected from hydrogen, methyl, ethyl, n-propyl, isopropryl, n-butyl and t-butyl.

In certain embodiments, $n_1$ is 0. In other embodiments, $n_1$ is 1.

In some embodiments, guanidine-containing compounds include cyclic guanidine-containing compounds having multicyclic, annulated and linked ring systems of formula (III):

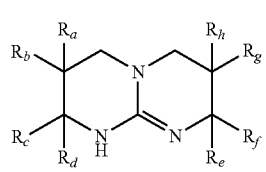

Formula (III)

where
$n_2$ and $n_3$ are are independently 0 or 1; and
each of $R^a$, $R^b$, $R^c$, $R^d$, $R^e$, $R^f$, $R^g$, $R^h$ is independently alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

where any two of $R^a$, $R^b$, $R^c$, $R^d$, $R^e$, $R^f$, $R^g$, $R^h$ together form a five-member or six-member ring.

In certain embodiments, each of $R^a$, $R^b$, $R^c$, $R^d$, $R^e$, $R^f$, $R^g$, $R^h$ is independently selected from hydrogen, substituted or unsubstituted $C_1$-$C_{12}$ alkyl, substituted or unsubstituted $C_1$-$C_{12}$ cycloalkyl, substituted or unsubstituted $C_1$-$C_{12}$ aryl, substituted or unsubstituted $C_1$-$C_{12}$ alkenyl and substituted or unsubstituted $C_1$-$C_{12}$ alkynyl.

In certain embodiments, each of $R^a$, $R^b$, $R^c$, $R^d$, $R^e$, $R^f$, $R^g$, $R^h$ is independently selected from hydrogen or substituted or unsubstituted $C_1$-$C_{12}$ alkyl.

In certain embodiments, each of $R^a$, $R^b$, $R^c$, $R^d$, $R^e$, $R^f$, $R^g$, $R^h$ is independently selected from hydrogen, methyl, ethyl, n-propyl, isopropryl, n-butyl and t-butyl.

In some embodiments $n_2$ is 0 and $n_3$ is 1; or $n_2$ is 1 and $n_3$ is 0; or $n_2$ is 0 and $n_3$ is 0; or $n_2$ is 1 and $n_3$ is 1.

The reagent composition may include one or more types of catalysts, depending on the type of polymer substrate and conditions employed during the subject methods (e.g., temperature or duration of treatment). In some embodiments, the reagent composition includes only a single type of catalyst. In other embodiments, the reagent composition includes two or more types of catalysts, such as three or more types, such as four or more types and including 5 or more types of catalysts. In some instances, the number of types of catalysts ranges, such as from 1 to 5 types of catalysts, such as 2 to 4 types of catalysts.

The amount of catalyst present in the subject reagent compositions may vary, depending on the specific contacting protocol, type of polymer and type of catalyst. In some embodiments, the amount of catalyst in the subject reagent compositions in 25% by weight or less, such as 20% by weight or less, such as 15% by weight or less, such as 10% by weight or less, such as 5% by weight or less, such 3% by weight or less, such as 2% by weight or less, such as 1% by weight or less, such as 0.5% by weight or less, such as 0.1% by weight or less and including 0.01% by weight or less.

In some embodiments, the reagent composition is a non-aqueous liquid composition. In certain instances, the reagent composition is solvent-free. By "solvent-free" is meant that the reagent composition does not include any additional solvents, where the nucleophilic reagent serves as both the solvent and the nucleophilic reagent. In some embodiments, the reagent composition consists of (i.e., only includes) nucleophilic reagent and catalyst. The reagent composition may be contacted with the surface of the polymer substrate by any convenient protocol, including but not limited to using a drop deposition technique (e.g., with a pipette, syringe with or without syringe pump), spraying, spin casting, swabbing, sponging, brushing, aspirating the reagent composition onto the polymer substrate surface, submerging all or part of the substrate into a volume of the reagent composition and combinations thereof, among other protocols. Where the polymer substrate is a surface of a container (e.g., test tube, syringe, pipettes, culture tube, petri dish, microtiter plate, flask, beaker, straw, catheter, cuvette, microtubes), the reagent composition may be contacted by filling all or part of the interior volume of the container with the reagent composition. All or part of the surface of the polymer substrate may be contacted with the reagent composition. For example, 10% or more of the polymer substrate surface may be contacted with the reagent composition, such as 20% or more, such as 30% or more, such as 40% or more, such as 50% or more, such as 60% or more, such as 70% or more, such as 80% or more and including contacting 90% or more of the polymer substrate surface with the reagent composition. In certain embodiments, the entire (i.e., 100%) surface of the polymer substrate is contacted with the reagent composition. Where desired, the contacted area of the polymer substrate may be in the form of discrete regions, such as in the form of a plurality of rows, quadrants, or an array of spots (e.g., dots, squares, etc.), or some other pattern on the surface of the polymer substrate.

Where the polymer substrate is a surface of a container, in certain instances, methods include contacting only the interior surface of the container with the reagent composition. As such, in these embodiments the interior surface of the container is made hydrophilic while the exterior surface remains hydrophobic. All or part of the interior surface of the container may be contacted with the reagent composition. For example, 10% or more of the interior surface of the container may be contacted with the reagent composition, such as 20% or more, such as 30% or more, such as 40% or more, such as 50% or more, such as 60% or more, such as 70% or more, such as 80% or more and including contacting 90% or more of the interior surface of the container with the reagent composition. In some embodiments, the entire (i.e., 100%) interior surface of the container is contacted with the reagent composition. In certain instances, the reagent composition may be contacted with the container only at discrete regions of the container, such as along a bottom portion of the interior surface of a test tube, along the rim of a beaker, flask, jar or bottle, at the tip of a syringe, at the pour spout of a liquid transfer container (e.g. a beaker), or in the form of a plurality of rows or array of spots (e.g., dots, squares, etc.).

In certain instances, all surfaces of the container are contacted with the reagent composition such that both the interior surface and the exterior surface of the container are converted from hydrophobic to hydrophilic.

The temperature at which the reagent composition is maintained in contact with the polymer substrate may vary depending on the type of polymer, size of the polymer substrate, extent of hydrophilicity desired and the duration the reagent composition is maintained in contact with the polymer substrate. In some embodiments, the reagent composition is maintained in contact with the polymer substrate at a temperature which ranges from 20° C. to 150° C., such as from 25° C. to 125° C., such as 30° C. to 100° C., such as 35° C. to 85° C. and including from 40° C. to 75° C. In certain embodiments, the reagent composition is maintained in contact with the polymer substrate at room temperature.

As described above, in practicing the subject methods the reagent composition is maintained in contact with the surface of the polymer substrate in a manner sufficient to convert the surface from hydrophobic to hydrophilic while retaining the mechanical and optical properties of the polymer substrate. In some embodiments, methods include maintaining the reagent composition in contact with the hydrophobic polymer substrate at a temperature sufficient to retain the mechanical and optical properties of the polymer substrate. In other words, methods of the present invention are carried out at temperatures where the polymer substrate does not melt, deform or otherwise lose any structural integrity. Depending on the type of polymer, size of substrate, reagent composition employed and duration of treatment, in some embodiments the reagent composition may be maintained in contact with the substrate at a temperature which is 5° C. or more below the glass transition temperature of the polymer substrate, such as 6° C. or more, such as 7° C. or more, such as 8° C. or more, such as 9° C. or more, such as 10° C. or more, such as 12° C. or more and including maintaining the reagent composition in contact with the polymer substrate at a temperature which is 15° C. or more below the glass transition temperature of the polymer substrate. For example, where the polymer substrate is a polyethylene terephthalate container, the reagent composition may be maintained in contact with the surface of the polyethylene terephthalate container at a temperature of 65° C. or lower, such as 60° C. or lower, such as 55° C. or lower and including 50° C. or lower, such as for example at room temperature.

The temperature may remain constant, or may be changed at one or more times during the subject methods. In some embodiments, the temperature is maintained at a constant temperature throughout the duration of the subject methods. In other embodiments, the temperature is raised one or more times. In other embodiments the temperature is reduced one or more times. In yet other embodiments, the temperature is both raised one or more times and reduced one or more times during the subject methods. Where the temperature is changed one or more times during the subject methods, the temperature change may take place at any time during the subject methods, as desired. For example, the change in temperature may proceed at regular intervals, such as by raising or lowering the temperature every 5 minutes, such as every 10 minutes, such as every 15 minutes, such as every 20 minutes, such as every 25 minutes, such as every 30 minutes and including every 60 minutes. In other instances, the change in temperature may be continuous (i.e., gradual) throughout the subject methods, such as by raising or lowering the temperature at a predetermined rate. For example, the temperature may be raised or lowered during the subject methods at rate ranging from 0.1° C. per minute to 5° C. per minute, such as from 0.25° C. per minute to 4.5° C. per minute, such as from 0.5° C. per minute to 4° C. per minute, such as from 0.75° C. per minute to 3.5° C. per minute and including raising or lowering the temperature at a rate ranging from 1° C. per minute and 3° C. per minute. In yet other instances, the temperature may be changed in accordance with a desired adjustment, as described in greater detail below. For example, in some instances if the physical shape of the polymer substrate is changing (e.g., a polymer container is becoming deformed), the temperature may be reduced, such as by 1° C. or more, such as 2° C. or more, such as by 5° C. or more and including reducing the temperature by 10° C. or more.

The reagent composition may be maintained in contact with the polymer substrate for any suitable duration so long as it is sufficient to convert at least a portion of the polymer substrate surface from hydrophobic to hydrophilic. Depending on the type of polymer, nucleophilic reagent, catalyst and temperature, the reagent composition may be maintained in contact with the polymer substrate for 5 minutes or more, such as for 10 minutes or more, such as for 15 minutes or more, such as for 20 minutes or more, such as for 30 minutes or more, such as for 45 minutes or more and including for 60 minutes or more. An upper limit for the duration the reagent composition is maintained in contact with the polymer substrate may, in certain instances be 60 minutes or less, such as 45 minutes or less, such as 30 minutes or less and including for 15 minutes or less.

In certain embodiments, methods include multiple contacting intervals. By "multiple contacting intervals" is meant that the polymer substrate is contacted with a reagent composition two or more times in sequential manner. As such, a first reagent composition is removed from contact with the polymer substrate and a second reagent is reapplied to the polymer substrate. In practicing the subject methods, protocols may include two or more contacting intervals, such as three or more contacting intervals, such as four or more contacting intervals and including five or more contacting intervals.

The duration between contacting intervals in a multiple contacting interval protocol may vary, depending on the size and type of polymer substrate as well as the properties of the modified polymer substrate desired. For example, the duration between contacting intervals in a multiple contacting protocol may be predetermined and follow at regular intervals. In these embodiments, the time between contacting intervals may be 5 minutes or longer, such as 10 minutes or longer, such as 15 minutes or longer, such as 30 minutes or longer, such as 45 minutes or longer and including 60 minutes or longer. An upper limit period of time between contacting intervals is, in some instances 24 hours or shorter, such as 12 hours or shorter, such as 8 hours or shorter, such as 4 hours or shorter and including 1 hours or shorter. In certain embodiments, the time between contacting intervals ranges such as from 5 minutes to 480 minutes, such as from 10 minutes to 360 minutes, such as from 15 minutes to 240 minutes and including from 30 minutes to 60 minutes.

Subsequent contacting intervals in multiple contacting interval protocols may employ the same or different formulation of reagent composition. In certain instances, a subsequent contacting interval may contain a different nucleophilic agent. In other instances, a subsequent contacting interval may contain a different catalyst. In yet other instances, a subsequent contacting interval may contain a different nucleophilic agent and a different catalyst. Where the same nucleophilic agent or catalyst are employed in a subsequent contacting interval, the concentration of nucleophilic agent or catalyst may be the same or different. For example, the concentration of nucleophilic agent or catalyst in subsequent contacting intervals may be increased by 10% or greater, such as 20% or greater, such as 50% or greater, such as 75% or greater, such as 90% or greater and including 100% or greater. An upper limit for the increase in concentration of nucleophilic agent and catalyst in subsequent dosage intervals is, in some instances, 10-fold or less, such as 5-fold or less, such as 2-fold or less, such as 1-fold or less, such as 0.5-fold or less and including 0.25-fold or less. On the other hand, the concentration of nucleophilic agent or catalyst may be decreased in subsequent contacting intervals, such as decreased by 10% or greater, such as 20% or greater, such as 50% or greater, such as 75% or greater, such as 90% or greater and including 100% or greater. An upper limit for the decrease in concentration of nucleophilic agent or catalyst in subsequent contacting intervals is, in some instances, 10-fold or less, such as 5-fold or less, such as 2-fold or less, such as 1-fold or less, such as 0.5-fold or less and including 0.25-fold or less.

The duration each subsequent reagent composition is maintained in contact with the polymer substrate in a multiple contacting interval protocol may be the same, different or a combination thereof depending on the number of contacting intervals in the protocol, the formulation of reagent composition, extent of desired surface hydrophilicity and type of polymer. In some embodiments, each reagent composition is maintained in contact with the polymer substrate for the same amount of time. For example, a multiple contacting interval according to these embodiments may include contacting the polymer substrate with first, second and third reagent compositions, each for a duration of 15 minutes (i.e., a first reagent composition for 15 minutes, followed by a second reagent composition for 15 additional minutes, followed by a third reagent composition for yet another 15 additional minutes). In other embodiments, each reagent composition is maintained in contact with the polymer substrate for different amounts of time. For example, a multiple contacting interval according to these embodiments may include contacting the polymer substrate with a first reagent composition for 35 minutes followed by a contacting the polymer substrate with a second reagent composition for an additional 15 minutes.

Likewise, subsequent contacting intervals in multiple contacting interval protocols may employ the same or different temperature or a combination thereof. In some embodiments, each reagent composition is maintained in contact with the polymer substrate at the same temperature. For example, a multiple contacting interval according to these embodiments may include contacting the polymer substrate with first, second and third reagent compositions, each at a temperature of 10° C. below the glass transition temperature of the subject polymer substrate.

In other embodiments, each reagent composition is maintained in contact with the polymer substrate at the different temperatures. In certain instances, a subsequent contacting interval may employ an increased temperature as compared to the previous contacting interval, such as an increase by 5° C. or more, such as 6° C. or more, such as 7° C. or more, such as 8° C. or more, such as 9° C. or more, such as 10° C. or more and including an increase by 15° C. or more. In other instances, a subsequent contacting interval may employ an reduced temperature as compared to the previous contacting interval, such as a reduction by 5° C. or more, such as 6° C. or more, such as 7° C. or more, such as 8° C. or more, such as 9° C. or more, such as 10° C. or more and including an increase by 15° C. or more. For example, a multiple contacting interval according to these embodiments may include contacting the polymer substrate with a first reagent composition at 10° C. below the glass transition temperature of the subject polymer substrate followed by a contacting the polymer substrate with a second reagent composition at room temperature.

In some embodiments, methods also include removing the reagent composition from contact with the surface of the polymer substrate. By "removing" the surface of the polymer substrate from contact with the reagent composition is meant that no amount of the reagent composition remains in contact with the polymer substrate, including any residual amount of reagent composition left behind on the surface. In other words, when the reagent composition is removed all traces of the reagent composition are no longer in contact with the surface of the polymer substrate, resulting in zero reactivity with the electrophilic backbone of the polymer substrate. In certain embodiments, removing the reagent composition from the surface of the polymer substrate includes washing any residual reagent composition from the surface of the polymer substrate. The polymer substrate may be washed by any convenient protocol, such as by washing with water, buffer, organic solvent or any other suitable liquid composition sufficient to remove any traces of the reagent composition from the polymer substrate. In certain instances, the polymer substrate may be washed using a liquid composition (e.g., water or buffer) with added heat or by ultrasound, among other washing protocols.

In certain embodiments, methods include monitoring changes in the contact angle of water on the surface of the polymer substrate or the surface energy over a period of time after the reagent composition has been removed from contact with the polymer substrate. In other words, methods may include determining the stability of the surface modification of the polymer substrate. In embodiments of the invention, the surface modification of the polymer substrate is non-leachable by a biological fluid. The term "biological fluid" as used herein refers to a material or mixture of material in liquid form isolated from an individual (including without limitation blood, plasma, serum, cerebrospinal fluid, lymph, tears, saliva, urine, semen, vaginal fluids, amniotic fluid, cord blood, mucus, synovial fluid, and tissue sections) as well as common aqueous buffers for diluting the aforementioned biological fluids. In some embodiments, surface modification according the subject methods exhibits little to no exudation of the transesterified polymer surface moieties. Surface modification according to the subject methods are also biocompatible. The term "biocompatible" is used herein in its conventional sense to refer to a material which, upon contact with a biological sample, does not elicit an adverse biological response (e.g., an inflammatory or other immunological response) which is detrimental to the biological sample. In other words, the surface modification has little, if any, effect on a biological sample. For example, the surface modification may cause degradation or incompatibility of a biological sample (e.g., whole blood, plasma, platelets, etc.) with the modified surface by 3% or less, such as 2.5% or less, such as 2% or less, such as 1.5% or less, such as 1% or less, such as 0.5% or less, such as 0.1% or less, such as 0.01% or less and including causing degradation or incompatibility of the biological sample with the modified surface by 0.001% or less. In certain embodiments, the surface modification is completely inert to a biological sample.

In monitoring the stability of the surface modification, the contact angle or the surface energy of the polymer substrate may be determined 1 hour or more after the reagent composition has been removed from contact from the polymer substrate, such as 2 hours or more, such as 4 hours or more, such as 8 hours or more, such as 12 hours or more, such as 16 hours or more, such as 24 hours or more, such as 48 hours or more, such as 72 hours or more, such as 96 hours or more, such as 120 hours or more, such as 144 hours or more and including determining the contact angle of water on the surface of the polymer substrate or the surface energy of the polymer substrate 168 hours or more after the reagent composition has been removed from contact from the polymer substrate.

In some embodiments, methods may also include ascertaining the chemical and physical properties of the polymer substrates. Ascertaining the chemical and physical properties of the polymer substrate may include, but is not limited to, determining the chemical composition of the polymer substrate surface (e.g., the extent of surface transesterification) as well as assessing physical properties of the polymer substrate, such as surface roughness, flexibility, hardness, optical properties (e.g., transparency), compressive modulus as well as contact angle made by water on the polymer substrate surface and surface energy, as described above. Methods for analyzing polymer substrates of interest may include Fourier transform infrared spectroscopy (FT-IR), UV-vis spectroscopy, atomic force microscopy (AFM), hardness presser, extensometers, contact angle goniometers, among other analytical protocols.

The chemical and physical properties of the polymer substrate may be ascertained at any time. In some instances, the chemical and physical properties of the polymer substrate are ascertained before contacting the reagent composition with the polymer substrate, such as for example, to determine the inherent (i.e., baseline) chemical and physical properties of the polymer substrate. In other instances, the chemical and physical properties of the polymer substrate may be ascertained before contacting the polymer substrate with the reagent composition and after the reagent composition has been removed from contact with the polymer substrate, such as for example to determine the change in the chemical and physical properties as a result of surface modification by the subject methods.

In certan embodiments, ascertaining the chemical and physical properties of the polymer substrate include determining that little to no depolymerization of the polymer has taken place as a result of surface modification by the subject methods. In these embodiments, methods may include determining that the polymer has depolymerized by 5% or less as a result of surface modification according to the subject methods, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including depolymerizing by 0.1% or less as a result of surface modification according to the subject methods. The subject methods, in certain instances, include determining that no depolymerization has taken place as a result of surface modification by the subject methods.

In other embodiments, methods include determining that little to no reduction in the performance of the polymer substrate has taken place as a result of surface modification by the subject methods. In these embodiments, methods may include determining that the performance of the polymer substrate is reduced by 5% or less as a result of surface modification according to the subject methods, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including a reduction in performance by 0.1% or less as a result of surface modification according to the subject methods. In certain embodiments, methods include determining that the performance of the polymer substrate has been entirely unaffected.

For example, where the polymer substrate is an evacuated test tube, methods may include determining that there is little to no reduction the ability of the evacuated test tube to retain a vacuum. In these embodiments, methods include determining that the subject methods has reduced the ability of the evacuated test tube to retain a vacuum by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and determining that the subject methods has reduced the the ability of the evacuated test tube to retain a vacuum by 0.1% or less. In certain instances, methods include determining that the the subject methods has had no effect (i.e., does not reduce at all) on the ability of the evacuated test tube to retain a vacuum.

In yet other embodiments, methods include determining that little to no degradation of the polymer substrate has taken place as a result of surface modification according to the subject methods. In these embodiments, methods may include determining that the polymer substrate has degraded by 5% or less as a result of surface modification according to the subject methods, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including degrading by 0.1%. The subject methods, in certain instances, include determining that no degradation has taken place as a result of surface modification according to the subject methods.

In some embodiments, methods include monitoring reaction of the nucleophilic reagent with the polymer substrate throughout the entire method. In some embodiments, monitoring includes collecting real-time data (e.g., FT-IR spectra, optical transparency) such as by employing a detector to monitor each parameter. In other embodiments, monitoring includes characterizing each polymer substrate at regular intervals, such as every 1 minute, every 5 minutes, every 10 minutes, every 30 minutes, every 60 minutes or some other interval. In other instances, methods include characterizing the chemical and physical properties of the polymer substrate before contacting the polymer substrate with the reagent composition and after the reagent composition has been removed from contact with the polymer substrate, such as for example to determine the change in chemical and physical properties in response to the subject methods.

In some embodiments, methods of the invention also include assessing the properties of the polymer substrate. By "assessing" is meant that a human (either alone or with the assistance of a computer, if using a computer-automated process initially set up under human direction), evaluates the chemical and physical properties data collected for the polymer substrate and determines whether the polymer substrate is suitable or unsuitable to continue on to the next step of processing. If after assessing that the polymer substrate is suitable, each polymer substrate may proceed to the following step without any further adjustments. In other words, methods according to these embodiments include a step of assessing the chemical and physical properties to identify any desired adjustments. For example, if the modified polymer substrate surface is determined to be suitable after maintaining the reagent composition in contact with the polymer substrate for a predetermined amount of time, the modified polymer substrate may proceed to a wash step, such as where all traces of the reagent composition are removed from contact with the modified polymer substrate surface.

On the other hand, if after assessing the chemical and physical properties, the polymer substrate is determined to be unsuitable, methods of the invention may include identifying and making any desired adjustments. For example, in some instances if the chemical composition of the polymer substrate surface is determined to be undesirable (e.g., insufficient surface transesterification), the polymer substrate may be contacted with the reagent composition for an additional period of time, such as 1 additional minute or more, such as 5 additional minutes or more, such as 10 additional minutes or more, such as 15 additional minutes or more, such as 30 additional minutes or more and including 60 additional minutes or more. Alternatively, where the chemical composition of the polymer substrate surface is determined to be undesirable, the polymer substrate may be contacted with a different reagent composition, such as for example a reagent composition which contains a different nucleophilic reagent, a different catalyst or different concentrations of the same nucleophilic reagent and catalyst. Still further, where the chemical composition of the polymer substrate surface is determined to undesirable, the polymer substrate may be contacted with the reagent composition under different conditions, such as for example at a higher temperature.

In another example, if a physical property of the polymer substrate is determined to be undesirable (e.g., shape of substrate is being deformed), the temperature while maintaining the reagent composition in contact with the polymer substrate may be reduced, such as by reducing the temperature by 1° C. or more, such as by 5° C. or more, such as by 10° C. or more, such as by 15° C. or more and including reducing the temperature by 20° C. or more.

Polymer Containers having a Hydrophilic Surface

Aspects of the invention also include polymer containers having a hydrophilic surface prepared by the subject methods. The term "hydrophilic" is used in its conventional sense to mean having a positive thermodynamic affinity for the interaction with polar solvents, including water, where the polymer surface is wettable by water (e.g., water forms a film rather than an aggregated bead). In some embodiments, hydrophilic polymer container surfaces of interest are characterized as having a decreased contact angle made by water with the modified hydrophilic surface as compared to the unmodified hydrophobic polymer surface. In some embodiments, hydrophilic polymer container surfaces of interest are characterized by a decreased contact angle made by water of 5° or more as compared to the unmodified hydrophobic polymer surface, such as 10° or more, such as 15° or more, such as 25° or more, such as 30° or more, such as 45° or more and including a decreased contact angle made by water of 60° or more as compared to the unmodified hydrophobic polymer surface. In some embodiments, polymer containers of interest have a surface that makes a contact angle with water that is less than 90°, such as 85° or less, such as 80° or less, such as 75° or less, such as 70° or less, such as 65° or less, such as 60° or less and including 55° or less. In certain embodiments, polymer containers of interest are characterized as having a surface which makes a contact angle with water that is substantially the same as glass.

In other embodiments, modified hydrophilic polymer container surfaces are characterized as having an increased surface energy as compared with the surface energy of an unmodified hydrophobic polymer surface. In some embodiments, hydrophilic polymer container surfaces of interest are characterized as having an increased surface energy of 5% or more as compared to an unmodified hydrophobic polymer container surface, such as 10% or more, such as 25% or more, such as 50%, such as 75% or more and including 99% or more. In certain embodiments, hydrophilic polymer container surfaces of interest are characterized as having an increased surface energy of 1.5-fold or more as compared to an unmodified hydrophobic polymer container surface, such as 2-fold or more, such as 3-fold or more, such as 4-fold or more and including 5-fold or more. In certain embodiments, polymer containers of interest are characterized as having a surface which has a surface energy that is substantially the same as glass.

In embodiments of the invention, the term "container" is used in its conventional sense to refer to a device which is configured to hold or transport a volume of liquid without leakage. Containers of interest, may include but are not limited to, blood collection tubes, including evacuated and non-evacuated tubes, test tubes, centrifuge tubes, culture tubes, microtubes, syringes, fluidic conduits, stents, medical tubing including intravenous drug delivery lines, blood transfusion lines, caps, pipettes, petri dishes, microtiter plates (e.g., 96-well plates), flasks, vials, beakers, straws, catheters, cuvettes, polymeric lenses, jars, cans, cups, bottles, rectilinear polymeric containers (e.g., plastic boxes), food storage containers, polymeric bags such as intravenous drug delivery bags, blood transfusion bags as well as large liquid storage containers such as drums and liquid storage silos, among other types of containers.

In certain embodiments, polymer containers having a hydrophilic surface prepared by the subject methods are polyester containers and include test tubes (e.g., blood collection tubes) of polyethylene terephthalate and derivatives thereof.

As described above, in embodiments of the present invention, only the surface of the polymer container is hydrophilic. By "only the surface" is meant that only electrophilic linkages positioned at or near the surface of the polymer container have been modified (e.g., transesterified) while the remaining polymer container structure retains unmodified electrophilic polymer linkages. Depending on the thickness of the container walls, type of polymer and conditions of reaction in preparing the subject container, the depth of surface modification may vary, such as 100 µm or less, such as 50 µm or less, such as 25 µm or less, such as 10 µm or less, such as 1 µm or less, such as 0.1 µm or less and including 0.01 µm or less. In embodiments of the invention, the thickness of the surface modification (i.e., hydrophilic surface) is substantially uniform over the entire area of the polymer container surface contacted with the reagent composition according to the methods described above. By uniform is meant that the thickness of the surface modification at any given place deviates from the average thickness of the surface modification by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including by 0.1% or less. In certain embodiments, the thickness of the surface modification (i.e., hydrophilic surface) is substantially the same over the entire modified surface area of the polymer container.

All or part of the polymer container surface may be hydrophilic. In some embodiments, the interior surface of the container is hydrophilic while the exterior surface is hydrophobic. In other embodiments, the exterior surface of the container is hydrophilic while the interior surface is hydrophobic. In yet other embodiments, both the interior and exterior surfaces of the container are hydrophilic. In some instances, discrete regions of the polymer container surface are hydrophilic, such as in the form of a plurality of rows, quadrants, or an array of spots, or some other pattern on the surface of the polymer container surface.

Where the interior surface of the polymer container is hydrophilic, all or part of the interior surface may be hydrophilic. For example, 10% or more of the interior surface of the container may be hydrophilic, such as 20% or more, such as 30% or more, such as 40% or more, such as 50% or more, such as 60% or more, such as 70% or more, such as 80% or more and including contacting 90% or more of the interior surface. In certain embodiments, the entire interior surface is hydrophilic. In certain instances, discrete regions of the container may be hydrophilic, such as along a bottom portion of the interior surface of a test tube, along the rim of a beaker, flask, jar or bottle, at the tip of a syringe, at the pour spout of a liquid transfer container (e.g. beaker), or in the form of a plurality of rows or array of spots on the interior surface of the container. In embodiments, containers of interest have a volume which varies greatly, ranging from $10^{-3}$ mL to $10^6$ mL, such as from $10^{-2}$ mL to $10^5$ mL, such as from $10^{-1}$ mL to $10^4$ mL and including a volume which ranges from 1 mL to $10^3$ mL.

Polymer containers according to embodiments of the invention include polymers having a backbone that contain electrophilic linkages. In some embodiments, the polymer may be a polyester, a polycarbonate, a polyurethane, including hompolymeric and multipolymeric forms. In certain embodiments, the polymer container is a polycarbonate container. In certain other embodiments, the polymer container is a polyester container. For example, non-porous hydrophobic polyester containers of interest may include, but are not limited to, containers made of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly (ethylene suberate); poly(alkylene sebacates) such as poly (ethylene sebacate); poly(ε-caprolactone) and poly(β-propiolactone); poly(alkylene isophthalates) such as poly (ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly ([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide).

In embodiments of the invention, polymer containers having a modified hydrophilic surface have substantially the same mechanical and optical properties as polymer containers having an unmodified hydrophobic surface.

In some embodiments, polymer containers of interest having a hydrophilic surface have a flexibility which deviates from the flexibility of polymer containers having unmodified hydrophobic surface by 5% or less, such as by 4% or less, such as by 3% or less, such as by 2% or less, such as by 1% or less and including by 0.5% or less. In certain embodiments, polymer containers of interest having a hydrophilic surface have a flexibility which is identical to the flexibility of polymer containers having unmodified hydrophobic surface.

In other embodiments, polymer containers of interest have a compressive modulus which deviates from the compressive modulus of polymer containers having unmodified hydrophobic surface by 5% or less, such as by 4% or less, such as by 3% or less, such as by 2% or less, such as by 1% or less and including by 0.5% or less. In certain embodiments, polymer containers of interest have a compressive modulus which is identical to the compressive modulus of polymer containers having unmodified hydrophobic surface.

In yet other embodiments, polymer containers of interest have a hardness which deviates from the hardness of polymer containers having unmodified hydrophobic surface by 5% or less, such as by 4% or less, such as by 3% or less, such as by 2% or less, such as by 1% or less and including by 0.5% or less. In certain embodiments, polymer containers of interest have a hardness which is identical to the hardness of polymer containers having unmodified hydrophobic surface.

In some embodiments, polymer containers of interest having a hydrophilic surface have a wall thickness which deviates from the wall thickness of polymer containers having unmodified hydrophobic surface by 5% or less, such as by 4% or less, such as by 3% or less, such as by 2% or less, such as by 1% or less and including by 0.5% or less. In certain embodiments, polymer containers of interest having a hydrophilic surface have a wall thickness which is identical to the wall thickness of polymer containers having unmodified hydrophobic surface.

In yet other embodiments, polymer containers of interest have optical transparency which deviates from the optical transparency of polymer containers having unmodified hydrophobic surface by 5% or less, such as by 4% or less, such as by 3% or less, such as by 2% or less, such as by 1% or less and including by 0.5% or less. In certain embodiments, polymer containers of interest have an optical transparency which is identical to the optical transparency of polymer containers having unmodified hydrophobic surface.

In still other embodiments, polymer containers of interest have a weight which deviates from the weight of polymer containers having unmodified hydrophobic surface by 5% or less, such as by 4% or less, such as by 3% or less, such as by 2% or less, such as by 1% or less and including by 0.5% or less. In certain embodiments, polymer containers of interest have a weight which is identical to the weight of polymer containers having unmodified hydrophobic surface.

Surface modification of non-porous polymer substrates (e.g., containers), according to embodiments of the present disclosure, is stable. By stable surface modification is meant that the modified surface of the non-porous polymer substrate exhibits little to no physical or chemical change for an extended period of time, such as showing little to no change for 1 day or more, such as 3 days or more, such as 7 days or more, such as 14 days or more, such as 30 days or more, such as 6 months or more, such as 12 months or more and including showing little to no change for 5 years or more. In other words, surface modified non-porous polymer substrates maintain a hydrophilicity, surface energy (e.g., as measured by a contact angle measurement test), thickness, weight, optical transparency, volume, etc. (as described above) which changes by 5% or less over the extended period of time, such as by 3% or less, such as by 1% or less, such as by 0.5% or less, such as by 0.1% or less, such as by 0.05% or less and including by 0.01% or less. In certain embodiments, surface modification of non-porous polymer substrates as described herein shows no detectable change over an extended period of time (e.g., no detectable changes for over one year)

Kits

Also provided are kits, where kits at least include one or more, e.g., a plurality of, the subject polymer containers having a hydrophilic surface, as described above. Kits may further include other components for practicing the subject methods, such as application devices (e.g., syringes or pipets) or solvents to wash the treated non-porous hydrophobic polymer substrates or to use during methods of the invention.

In some embodiments, reagent compositions having an amount of one or more nucleophilic reagents (e.g., ethylene glycol, glycerol, etc.) and one or more catalysts (e.g., potassium hydroxide, 1,1,3,3-tetramethylguanidine) in combination with the subject non-porous hydrophobic polymer substrates (e.g., polycarbonate test tube, polycarbonate blood collection tube, PET test tube, PET blood collection tube, bottle, 96-well microtiter plate, culture tube, etc.) may be provided as a packaged kit.

In addition, kits may also include instructions for how to practice the subject methods, such as instructions for how to contact the non-porous hydrophobic polymer substrate with the reagent composition and conditions for maintaining the reagent composition in contact with the non-porous hydrophobic polymer substrate to convert at least a portion of the surface of the non-porous hydrophobic polymer substrate from hydrophobic to hydrophilic. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

Methods for modifying non-porous hydrophobic polymer substrates according to the present disclosure and polymer containers having modified hydrophilic surfaces find use in any application that would benefit from a polymeric substrate having a hydrophilic surface. Likewise, the subject methods also find use in any application which would benefit from controlled surface modification of a hydrophobic polymeric surface.

In certain examples, methods of the invention find use in modifying the interior surface of medical laboratory and pharmaceutical containers where assays and collected specimen samples would benefit from the reduction in interference provided by a hydrophilic surface, yet enable safe handling without the risk of broken glass from traditional borosilicate glassware.

In other examples, methods of the invention find use in modifying hydrophobic surfaces under controlled conditions to produce hydrophilic surfaces with little to no changes in the mechanical or optical properties of the polymer substrates. As such, the subject methods would benefit any no. 366703; lot 2160209). Glass tubes are considered the controls in this study because this type has been the standard device for collecting serum samples for over five decades. In addition, the glass tubes contain no clot activator, internal tube coating, or separator gel. The composition and additives for the glass, Vacuette™, PRT, RST, and SST™ tubes are shown in Table 1. All blood collection tubes were used before their expiration dates.

TABLE 1

Sources and characteristics of the blood collection tubes examined

| Tube | Tube dimensions (mm) | Draw volume (mL) | Wall material | Separator gel | Surfactant | Clot activator | Stopper lubricant |
|---|---|---|---|---|---|---|---|
| Glass (red-top) | 16 × 100 | 10.0 | Glass (borosilicate) | None | None | None | Glycerin |
| Vacuette (gold-top) | 13 × 75 | 4.0 | Plastic (PET) | Olefin oligomer[b] (white-opaque) | Unknown | Silica | Silicone |
| Plain red-top (red-top) | 13 × 100 | 5.0 | Plastic (PET) | None | Unknown | Silica | Silicone |
| Rapid serum tube (orange-top) | 13 × 100 | 5.0 | Plastic (PET) | Polymer gel[c] | Polyalkylene oxide modified poly-dimethylsiloxane[e] | Thrombin[c,d] | Unknown |
| SST (gold-top) | 13 × 75 | 3.5 | Plastic (PET) | Polymer gel[e,f] (yellow opaque) | Silwet L-720[g] | Silica | Silicone | application where there is need or desire to convert a polymer surface from hydrophobic to hydrophilic without compromising structural integrity, mechanical durability or any other physical property.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Materials and Methods
Materials and Supplies

Ethylene glycol (EG), potassium hydroxide (KOH), 1,5,7-Triazabicyclo[4.4.0]dec-5-ene (TBD) and 1,1,3,3-tetramethylguanidine (TMG) were purchased from Sigma-Aldrich. The following types of evacuated BCTs were examined in this study: (1) a plastic Vacuette™ (Greiner Bio-One™, gold-top tube with gel separator; 13×75 mm, cat. no. 454228; lot B091209); (2) a glass tube (BD, red-top Vacutainer™ no-additive blood tube; 16×100 mm, cat. no. 366441; lot 2219385); (3) a plastic SST™ tube (BD, gold-top Vacutainer™ tube with gel separator; 13×75 mm, cat. no. 367983; lot 2258708); (4) a plastic RST™ tube (BD, orange-top Vacutainer™ tube with gel separator; 13×100 mm, cat. no. 368774; lot 120804); (5) a plastic plain red-top (PRT) tube (BD, Vacutainer™ tube with no gel separator; 13×100 mm, cat. no. 367814; lot 2200653). Chemically modified tubes were made from unmodified PET tubes (BD, 3-mL Vacutainer® tubes with no interior coating; 3 mL, cat.

Surface Modification of Polyester Test Tubes and Characterization

Base catalyst (KOH, TBD, or TMG) was dissolved in EG at specified concentrations. 5 mL of catalyst-containing EG solution was poured into each tube and a batch of tubes were incubated at either room temperature (22° C.) or in a 55° C. water bath for specified durations. After incubation, EG solution was collected for repeated use and the tubes were cleansed with deionized water, dried by blowing with pressurized air, and evacuated after replacing the stopper. To assess hydrophilicity of the modified surface, the meniscus of 1 mL of deionized water within a tube was observed and the contact angle of a water droplet on the inner tube surface was measured.

Volatile Screen of Modified Polyethylene Terephthalate Tubes 18 specimens from different tube types prepared by surface modification of PET according to methods of the invention described above were sent to Mayo Medical Lab for volatile screening. All specimens had no detectable volatiles for clinical purposes (detection limit: 10 mg/dL). The volatiles examined were: methanol, isopropanol, ethanol, acetone, and ethylene glycol. These results demonstrate that there was no leaching of the surface modification from the polymer substrate prepared by the subject methods.

Determination of serum $TT_3$, $TT_4$, and Cortisol Concentrations

Quality control (QC) materials were poured and mixed for 30 minutes in each type of blood collection tube. All QC materials from the different tube types were transferred into 13×75 mm plastic test tubes. The samples were capped at room temperature if they were tested within 4 hours. Alternatively, they were stored between testing intervals at −70° C. for up to 7 days. $TT_3$, $TT_4$, and cortisol were shown in our laboratory to be stable for 7 days at −70° C. After pouring and mixing the QC material from 6 different types of blood collection tubes, serum immunoassay analyte levels were measured in random order on an Immulite™ 1000 Analyzer, according to the manufacturer's instructions.

Total thyroxine and triiodothyronine and cortisol were measured by competitive immunoassays using limited immobilized antibodies and labeled hormones. Briefly, the Siemens Immulite is a solid-phase competitive chemiluminescent immunoassay. The solid phase, a polystyrene bead, is coated with a mouse monoclonal antibody specific to either thyroxine, triiodothyronine, or cortisol. Thyroxine, triiodothyronine, and cortisol in the quality control material or patient's serum sample and an alkaline phosphatase conjugated to either thyroxine, triiodothyronine, or cortisol compete for a limited number of antibody sites on the polystyrene beads. After a washing step, a chemiluminescent substrate, adamantyl 1,2-dioxetane phosphate, is added. Following incubation, the chemiluminescent substrate is hydrolyzed by alkaline phosphatase bound to the polystyrene beads to yield an anion, which decomposes and emits photons of light. The photon output is inversely proportional to the concentration of thyroxine, triiodothyronine, or cortisol in the patient's sample. During the study, one reagent lot and one calibrator lot were used for the Immulite™ 1000 analyzer.

For patient samples, blood from 5 volunteers were collected via a syringe and 2 mL of whole blood from the syringe was slowly dripped into 5 different blood collection tubes. The samples were then analyzed in triplicates per patient using the same protocol described above for the QC materials.

Routine Chemistry Analytes

Routine chemistry analytes, that is, a comprehensive metabolic panel (Met C) from quality control material or patient's serum collected in the different tube types, was measured on a Siemens Dimension RxL™ Max analyzer (Siemens). A comprehensive metabolic panel contains the following analytes: albumin, alkaline phosphatase (ALP), alanine aminotransferase (ALT), aspartate aminotransferase (AST), urea nitrogen, total calcium, chloride, creatinine, total carbon dioxide, glucose, potassium, sodium, total bilirubin, and total protein. The quality control material and serum specimens were analyzed singly in random order and in the same analytical run. None of the routine clinical chemistry analytes examined showed any statistically or clinically significant differences in the general chemistry analyte concentrations in quality control material and patient's serum specimens among the blood collection tube types. (see FIGS. 10 and 11)

Mass Spectrometric Analysis with No-Testosterone Calibrator Sample

50 μL of internal standard (IS) (final concentration 400 ng/dL) was added to 200 μL of calibrator sample and incubated for 20 min at room temperature (RT). Next, a liquid-liquid extraction was performed using 1 mL of tert-butyl methyl ether. The collected organic phase was evaporated and the residue reconstituted in 150 μL water-methanol solution (1:1 ratio). Reverse phase LC was performed using a Kinetex C18 column (2.6 μm, 100×3 mm, Phenomenex). The flow-rate was kept constant at 0.45 mL/min and 30% mobile phase A combination of 0.1% formic acid in water and 70% mobile phase B (0.1% formic acid in methanol) was used as the starting liquid phase condition. After 1 min, mobile phase B was increased linearly to 95% in 2 min and left at 95% for another 1.5 min. Thereafter the system was reset to starting condition and allowed to equilibrate for 2 min, with a total run time of 5.5 min. For MS/MS analyses, electrospray ionization (ESI) run in positive mode, and multiple reaction monitoring (MRM) were performed on an API 5000 Mass Spectrometer (AB Sciex) with the following parameters: collision induced dissociation 9.00, curtain gas 40.0, nebulizer gas 50.0, heater gas 50.0, interface heater on at 650.0° C., ion spray voltage 3500 V. For quantitation, the 289.4>97.1 and 289.4>109.1 mass transitions (with dwell time of 50 ms) were used for testosterone and 292.4>97.0, or 292.4>109.2 for testosterone-d3 (IS). A calibration curve was established by testosterone standard solution (Cerilliant) spiked in double charcoal-stripped serum (BioChemed Services). For identification of interference from blood collection tubes, we first incubated them with zero calibrator for 6 hours at room temperature followed by centrifugation and further sample preparation. The source of the interference was investigated by separately incubating tube coating, stopper or separator gel with zero calibrator in clean glass tubes, followed by sample preparation and LC-MS/MS analysis.

Results and Discussion

Transformation of PET Surface via Base-catalyzed Glycolysis

FIGS. 1a and 1b depict water meniscus formed with the inside surface of an unmodified PET test tube having a hydrophobic interior surface (FIG. 1a) and a test tube which has been modified in accordance with the subject methods described above (FIG. 1b). In contrast to the unmodified PET test tube, the chemically modified tube exhibits a meniscus similar to one observed in a glass (borosilicate) test tube demonstrating that the interior surface of the modified PET test tube exhibits a greater hydrophilicity as compared to unmodified PET test tubes. In particular, the contact angle made by water with the modified interior surface is decreased as compared to the unmodified test tube surface shown in FIG. 1a. Likewise, the surface energy of the modified interior surface is increased as compared to the unmodified test tube surface. A comparison of FIGS. 1a and 1b demonstrate that the subject methods have no effect on the mechanical and optical properties of the test tubes shown. Analysis of the test tubes indicated that no depolymerization, no degradation and no change performance in containing an aqueous solution was detected.

Figure 2:
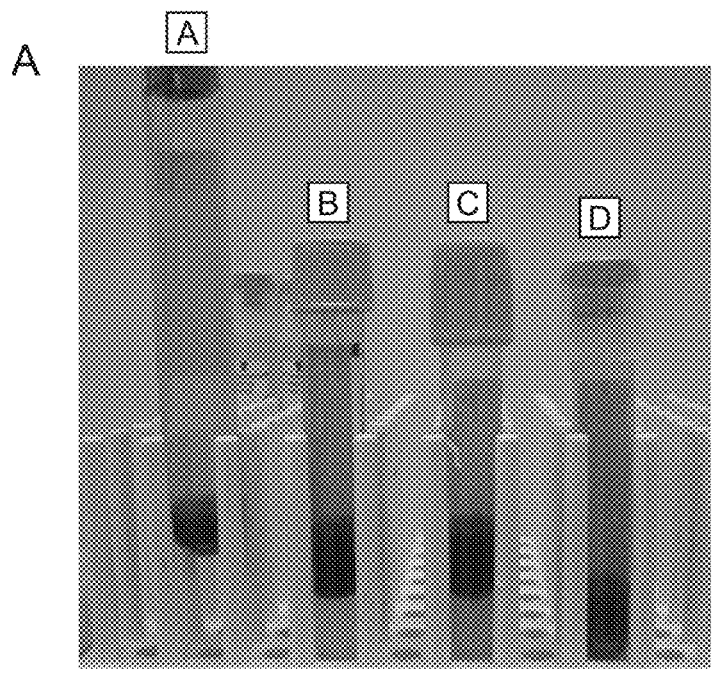
FIGS. 2a-b show an example of visual comparison of red blood cells before and after centrifugation in different types of test tubes and a polyester test tube modified according to the subject methods in certain embodiments.
Figure 2:
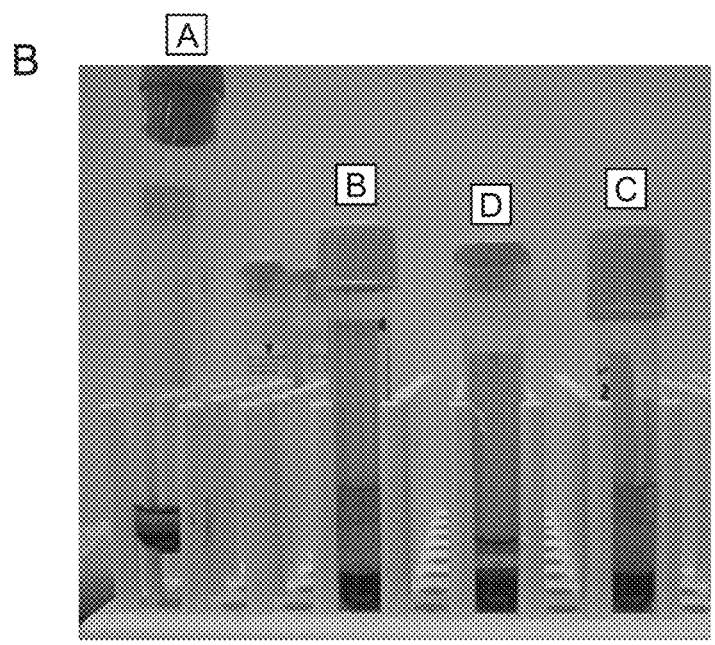

FIGS. 2a and 2b demonstrate a comparison of affinity of red blood cells with the surface of a serum tube. FIG. 2a depicts four types of test tubes: a) a glass serum tube (A); b) a Greiner polyethylene terephthalate serum tube (B); c) a Becton-Dickinson polyethylene terephthalate serum tube (C); and d) a polyethylene terephthalate serum tube (D) modified by the subject methods. An equivalent amount of red blood cells were deposited into the serum tubes and adhesion of red blood cells to the interior surface was visualized before centrifugation. (FIG. 2a) Each of the serum tubes with red blood cells were centrifuged and adhesion of red blood cells to the interior surface was again visualized after centrifugation (FIG. 2b) Comparison of adhesion of red blood cells to the interior surface of the serum tubes showed no different between adhesion of red blood cells to the modified polyethylene terephthalate serum tube before and after centrifugation, indicating that polyethylene terephthalate serum tubes modified by the subject methods can be employed for blood storage and serum separation applications. Also, serum tube (D) in FIGS. 2a and 2b demonstrates that surface modification provided by the subject methods are biocompatible showing no red blood cell adherence as well as no hemolysis of the serum layer.

Test of Analytical Bias using Quality Control Materials and Patient Blood Samples The quality of a polyester (e.g., PET) test tube which has been modified in accordance with the subject methods was compared with the commercial products widely used in clinical labs, using two different types of blood samples: QC materials and blood samples from 5 healthy volunteers. The concentrations of three types of analytes (cortisol, $TT_3$ and $TT_4$) were determined and compared against the values obtained from glass tubes. Glass is regarded as the standard container material for blood analysis; therefore, the deviations of concentration values from those obtained with glass tubes are indicative of interference caused by plastic tubes and their additives. Table 2 summarizes the results.

For QC materials, a polyester (e.g., PET) test tube which has been modified in accordance with the subject methods and Greiner tubes show significantly lower relative biases (+1.9% and +5.1% for cortisol; −3.3% and −2.2% for $TT_3$; −5.0% and −2.5% for $TT_4$, respectively) than BD tubes (e.g., for SST, +19.4% for cortisol; +15.0% for $TT_3$; +21.4% for $TT_4$, respectively). The positive bias values observed from BD tubes, which are consistent with previous findings,[2,3] are larger than desirable bias values based on biological variation[5]: 12.5%, 4.8%, and 3.0% for cortisol, $TT_3$, and $TT_4$, respectively. For patient blood samples, a polyester (PET) test tube which has been modified in accordance with the subject methods and Greiner tubes again show significantly lower relative biases (−3.8% and −1.2% for cortisol; +5.7% and +7.9% for $TT_3$; +0.2% and −2.7% for $TT_4$, respectively) than BD tubes (e.g., for SST, +5.9% for cortisol; +17.0% for $TT_3$; +12.9% for $TT_4$, respectively).

Thus, a polyester (e.g., PET) test tube which has been modified in accordance with the subject methods tubes show much less biases than BD tubes, and similar level of biases to Greiner tubes.

K-04 (2013) proficiency testing survey material from College of American Pathologist (CAP; CAP Northfield, Ill.), which was reconstituted according to instructions, and processed in the six different blood collection tubes (1 mL per tube) were also measured for $TT_3$, $TT_4$, and cortisol on the Immulite 1000 analyzer.

TABLE 2

Comparison of immunoassay test results from polyester test tubes modified in accordance with the subject methods (e.g., surface modified polyethylene terephthalate) and examples of commercially available test tubes (a) Cortisol

|  | QC material (n = 9) | | Patient blood (n = 5) | | Proficiency K-04 (n = 3) (2013) | |
| --- | --- | --- | --- | --- | --- | --- |
|  | Mean ± S.E. (µg/dL) | Bias | Mean ± S.E. (µg/dL) | Bias | Mean ± S.E. (µg/dL) | Bias |
| Becton Dickinson Glass | 42.8 ± 0.6 |  | 8.8 ± 0.9 |  | 11.1 ± 0.7 |  |
| Surface-Modified Polyethylene Terephthalate according to the Subject Methods | 43.6 ± 0.5 | +1.9% | 8.5 ± 0.9 | −3.8% | 11.3 ± 0.5 | +1.8% |
| Becton Dickinson Serum Separator Tube (SST) | 51.1 ± 0.7 | +19.4% | 9.3 ± 0.9 | +5.9% | 11.5 ± 0.6 | +3.6% |
| Becton Dickinson Rapid Serum Tube (RST) | 52.8 ± 1.2 | +23.4% | 9.4 ± 1.0 | +6.1% | 11.5 ± 0.6 | +3.6% |
| Becton Dickinson Plain Red Top Tube | 47.1 ± 0.5 | +10.0% | — | — | 12.4 ± 0.2 | +11.7% |
| Greiner PET tube% | 45.0 ± 0.7 | +5.1% | 8.7 ± 0.9 | −1.2% | 11.4 ± 0.5 | +2.7% |

The results are mean of triplicate measurements.
No significant differences in cortisol concentrations among tube types were observed (F = 0.68; p = 0.667)
Cortisol desirable bias based on biological variation is +/−10.26

(b) $TT_3$ (total triiodothyronine)

|  | QC material (n = 9) | | Patient blood (n = 5) | | Proficiency K-04 (n = 3) (2013) | |
| --- | --- | --- | --- | --- | --- | --- |
|  | Mean ± S.E. (ng/dL) | Bias | Mean ± S.E. (ng/dL) | Bias | Mean ± S.E. (µg/dL) | Bias |
| Becton Dickinson Glass | 359 ± 5 |  | 83.5 ± 3.0 |  | 143.6 ± 3.1 |  |
| Surface-Modified Polyethylene Terephthalate according to the Subject Methods | 347 ± 5 | −3.3% | 88.2 ± 3.7 | +5.7% | 139.5 ± 5.0 | −2.9% |

TABLE 2-continued

Comparison of immunoassay test results from polyester test tubes modified in accordance with the subject methods (e.g., surface modified polyethylene terephthalate) and examples of commercially available test tubes

| | | | | | | |
|---|---|---|---|---|---|---|
| Becton Dickinson Serum Separator Tube (SST) | 413 ± 10 | +15.0% | 97.6 ± 2.4 | +17.0% | 141.7 ± 4.6 | −1.3% |
| Becton Dickinson Rapid Serum Tube (RST) | 406 ± 5 | +13.1% | 91.9 ± 3.9 | +10.1% | 142.3 ± 2.4 | −0.9% |
| Becton Dickinson Plain Red Top Tube | 379 ± 3 | +5.6% | — | — | 146.3 ± 2.6 | 1.9% |
| Greiner PET tube | 351 ± 6 | −2.2% | 90.1 ± 2.6 | +7.9% | 137.7 ± 2.8 | −4.1% |

The results are mean of triplicate measurements.
No significant differences in $TT_3$ concentrations among tube types were observed (F = 0.70; p = 0.653)
Cortisol desirable bias based on biological variation is +/−3.53%

(c) $TT_4$ (thyroxine)

| | QC material (n = 9) | | Patient blood (n = 5) | | Proficiency K-04 (n = 3) (2013) | |
|---|---|---|---|---|---|---|
| | Mean ± S.E. (µg/dL) | Bias | Mean ± S.E. (µg/dL) | Bias | Mean ± S.E. (µg/dL) | Bias |
| Becton Dickinson Glass | 15.9 ± 0.4 | | 6.1 ± 0.3 | | 4.9 ± 0.2 | |
| Surface-Modified Polyethylene Terephthalate according to the Subject Methods | 15.1 ± 0.3 | −5.0% | 6.1 ± 0.3 | +0.2% | 4.8 ± 0.2 | −2.0% |
| Becton Dickinson Serum Separator Tube (SST) | 19.3 ± 0.4 | +21.4% | 6.9 ± 0.5 | +12.9% | 5.1 ± 0.2 | +4.1% |
| Becton Dickinson Rapid Serum Tube (RST) | 20.1 ± 0.4 | +26.4% | 6.3 ± 0.4 | +3.5% | 5.1 ± 0.2 | +4.1% |
| Becton Dickinson Plain Red Top Tube | 17.2 ± 0.2 | +8.2% | — | — | 6.0 ± 0.7 | +22.4% |
| Greiner PET tube | 15.5 ± 0.2 | −2.5% | 5.9 ± 0.3 | −2.7% | 4.9 ± 0.2 | 0.0% |

The results are mean of triplicate measurements.
No significant differences in $TT_4$ concentrations among tube types were observed (F = 1.97; p = 0.0772)
$TT_4$ desirable bias based on biological variation is +/−3.00%

Tube Comparisons of Cortisol, $TT_3$, and $TT_4$ Concentrations from CAP K-04 PT Survey Material The effect of pouring CAP K-04 (2013) survey material in poured and mixed in the six different tube types on cortisol, $TT_3$, and $TT_4$ concentration was tested. Compared to glass tubes, no significant difference in cortisol, $TT_3$ and $TT_4$ concentrations from surface modified test tubes of interest with the CAP K-04 (2013) survey material was found. In contrast, the CAP K-04 (2013) survey material cortisol, $TT_3$ and $TT_4$ concentrations in RST and SST tubes were significantly higher compared to glass tubes. The PRT compared to the glass tubes showed significantly higher cortisol and TT4 results. The PRT TT3 results were higher compared to glass tubes. These results demonstrate that the test tubes having surface modifications according to the subject methods behave like glass test tubes.

Test of Analytical Bias using No-testosterone Calibrator Sample

Figure 3B:
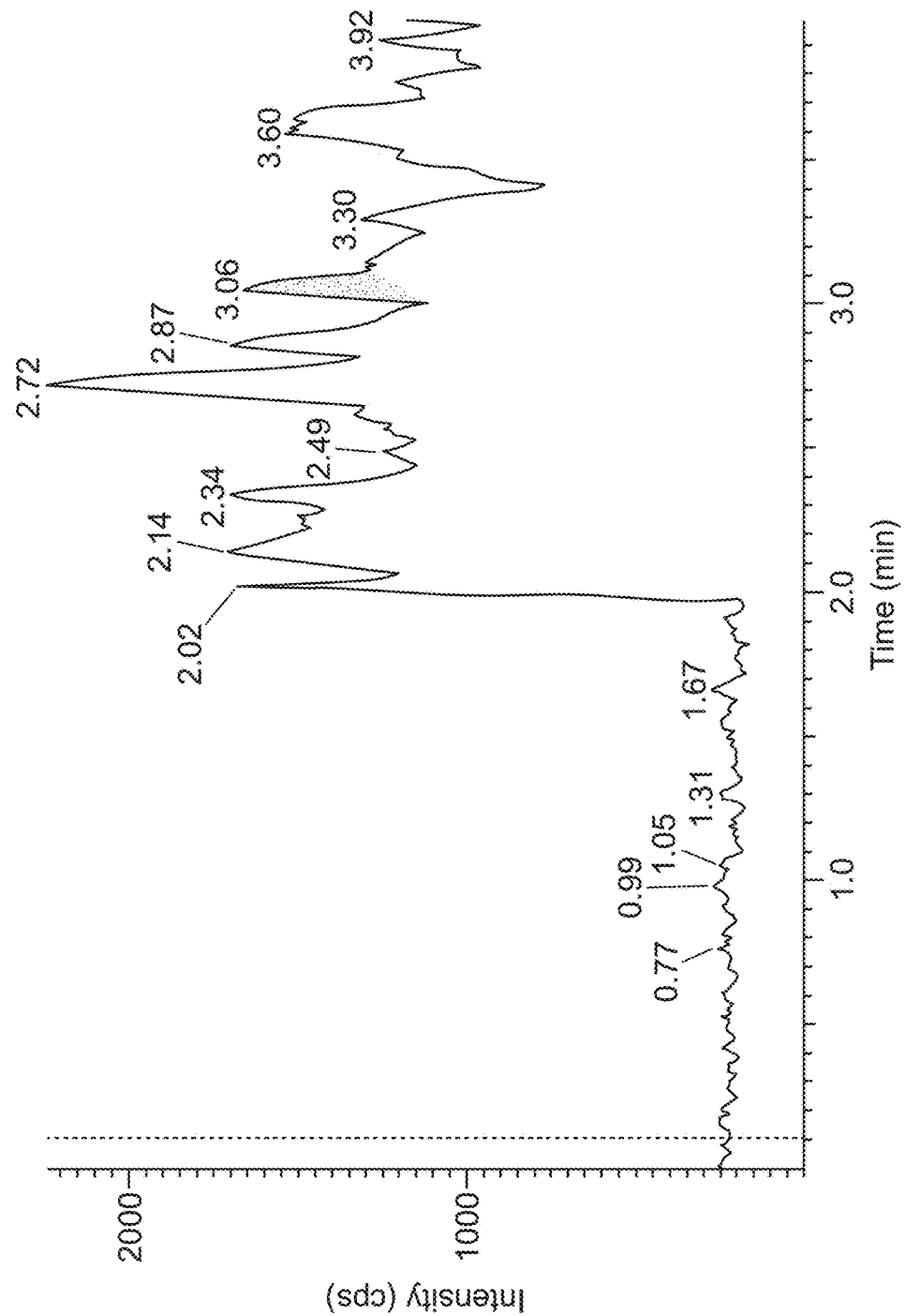
Figure 3C:
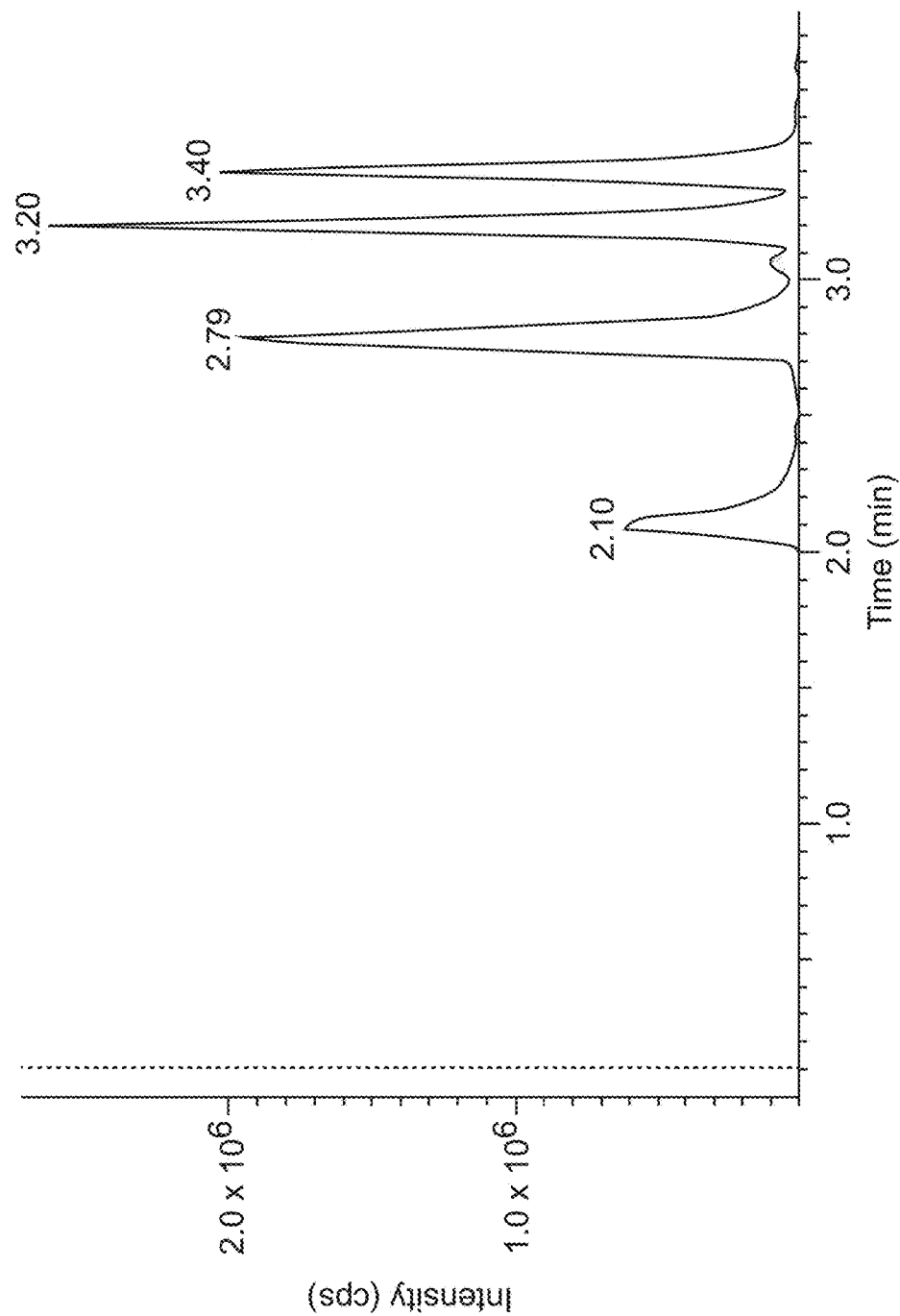

More clinical labs are adopting mass spectrometry to improve accuracy, analyte specificity, and sensitivity of their assays. The quality of a polyester (e.g., PET) test tube which has been modified in accordance with the subject methods and other commercial blood collection tubes in terms of surface interference with mass spectrometry-based chemical analysis was assessed by incubating calibrator samples containing no testosterone (i.e., negative controls) in the tubes and then performing a liquid chromatography-mass spectrometry (LC-MS) analysis. The results are compared in FIG. 3. FIG. 3 shows deconvoluted chromatograms from LC-MS analyses of no-testosterone calibrator samples in three different types of test tubes. FIG. 3a shows results in glass test tubes. FIG. 3b shows results in surface-modified polyethylene terephthalate test tubes prepared according to embodiments of the invention. FIG. 3c shows results from Becton Dickinson Serum Separator Tubes (BD SST)

As expected with negative control samples, both glass and polyester (e.g., PET) test tubes which have been modified in accordance with the subject methods tubes exhibit normal background noise-level signals at the m/z peak (289.4>97.1) that is specific to the testosterone molecule. In contrast, the signals from BD SST tubes increased by a factor of $10^3$ with the neighboring peaks overwhelming the actual signal from real testosterone molecules, which is consistent with previously reported problems with this specific type of tubes. Such a false-positive result can lead to repeated tests and irreproducible results, if not wrong diagnosis based on erroneous test results.

This above results demonstrate that the interior surface of polyester blood collection tubes prepared according to the subject methods can render polyester surfaces to have glass-like properties on the inside of a container. The test results for immunoassays using QC materials and patient blood samples demonstrated excellent performance of surface modified tubes as compared to those tested above. These results also demonstrate that there was no leaching of the surface modification from the polymer substrate prepared by the subject methods.

Example 2

Materials and Methods

Surface Modification and Characterization.

Ethylene glycol (EG), potassium hydroxide (KOH), 1,5,7-triazabicyclo[4.4.0]dec-5-ene (TBD) and 1,1,3,3-tetramethylguanidine (TMG) were purchased from Sigma-Aldrich (St. Louis, Mo.). Glycerol (GL) (>99.5% pure) was obtained from Invitrogen (Carlsbad, Calif.). 1×1 inches flat plastic pieces were cut from square bottles or flat panels for the following plastic types: (1) PET (Corning cat. #46-000-CM, Corning, N.Y.), (2) PET glycol-modified (PETG, a variant of PET with an additional monomeric unit of 1,4-cyclohexanedimethanol) (Nalgene cat. #2019-0500, Penfield, N.Y.), (3) PC (Corning cat. #431430, Corning, N.Y.), and (4) PS (polystyrene sheet, Columbus, Ohio). PS pieces were immersed into n-hexane to remove residual adhesives or coatings. Base catalyst (KOH, TBD, or TMG) was dissolved in EG at specified concentrations (20-40%). 5 mL of catalyst-containing EG solution was poured into reaction chambers containing 1×1 inches square plastic pieces or into each blood collection tube. Then, a batch of plastic materials was incubated at either room temperature (22° C. for PET, PETG, PS) or in a 55-60° C. incubator (for some PET tubes and PC) for specified durations. After incubation, the EG solution was collected for repeated use and the plastic samples were rinsed with deionized water and dried by blowing with a stream of filtered air.

For FT-IR measurements, flat PET plaques were placed in contact with 20%(v/v) TMG solution made in EG, incubated at room temperature for 2 hours, rinsed with deionized water, and then dried inside an over (40° C.) for 6 hours to remove any trace amount of water on the surface. Attenuated total reflection (ATR) mode was used to detect changes at the surface of the plastics using an FT-IR spectrometer (VERTEX 70, Bruker Optics Inc., Billerica, Mass.).

To assess hydrophilicity of the modified surface, the contact angle was measured by recording digital images of a water droplet on a flat plastic surface or an air bubble captured under water using a contact angle goniometer (model 100-F0, ramé-hart instrument co., Succasunna, N.J.). The obtained images were analyzed by fitting with the DROPimage software (version 2.0.05) provided by the manufacturer. Measurements for each plastic type were repeated 5 times for averaging. Welch's t-test was used for assessing statistical significance of the changes in contact angles.

PET Blood Collection Tubes Used.

The following types of evacuated blood collection tubes were examined in this study: (1) a plastic Vacuette™ (Greiner Bio-One™, gold-top tube with gel separator; 13×75 mm, cat. no. 454228; lot B091209, Monroe, N.C.); (2) a glass tube (Becton Dickinson (BD, Franklin Lakes, N.J.), red-top Vacutainer™ no-additive blood tube; 16×100 mm, cat. no. 366441; lot 2219385 from BD); (3) a plastic SST™ tube (BD, gold-top Vacutainer™ tube with gel separator; 13×75 mm, cat. no. 367983; lot 2258708); (4) a plastic RST™ tube (BD, orange-top Vacutainer™ tube with gel separator; 13×100 mm, cat. no. 368774; lot 120804); (5) a plastic plain red-top (PRT) tube (BD, Vacutainer™ tube with no gel separator; 13×100 mm, cat. no. 367814; lot 2200653). Chemically modified tubes were made from unmodified PET tubes (BD, 3-mL Vacutainer™ tubes with no interior coating; 3 mL, cat. no. 366703; lot 2160209).

Glass tubes were used as controls. The glass tubes contain no clot activator, internal tube coating, or separator gel. The composition and additives for the glass, Vacuette™, PRT, RST, and SST™ tubes are shown in Table 3. All blood collection tubes were used before their expiration dates.

TABLE 3

Characteristics of blood collection tubes

| Tube | Tube dimensions (mm) | Draw volume (mL) | Wall material | Separator gel | Surfactant | Clot activator | Anti-coagulant |
|---|---|---|---|---|---|---|---|
| Glass (red-top) | 16 × 100 | 10.0 | Glass (borosilicate) | None | None | None | None |
| ChemoPET | 13 × 75 | 3.0 | Chemically modified Plastic (PET) | None | None | None | None |
| Vacuette (gold-top) | 13 × 75 | 4.0 | Plastic (PET) | Olefin oligomer (white-opaque) | Unknown | Silica | None |
| Plain red-top (PRT) (red-top) | 13 × 100 | 5.0 | Plastic (PET) | None | Unknown | Silica | None |

TABLE 3-continued

Characteristics of blood collection tubes

| Tube | Tube dimensions (mm) | Draw volume (mL) | Wall material | Separator gel | Surfactant | Clot activator | Anti-coagulant |
|---|---|---|---|---|---|---|---|
| Rapid serum tube (RST) (orange-top) | 13 × 100 | 5.0 | Plastic (PET) | None | Polyalkylene oxide modified poly-dimethylsiloxane | Thrombin | None |
| SST (gold-top) | 13 × 75 | 3.5 | Plastic (PET) | Polymer gel (yellow opaque) | Silwet L-720$^g$ | Silica | None |

Chemical Analysis of Quality Control (QC) Materials and Patient Blood Samples. QC materials were poured and mixed for 30 minutes in each type of blood collection tube. All QC materials from the different tube types were transferred into 13×75 mm plastic test tubes. The samples were capped at room temperature if they were tested within 4 hours. Alternatively, they were stored between testing intervals at 4° C. for up to 7 days. The thyroid hormones, triiodothyronine ($TT_3$), thyroxine ($TT_4$), and cortisol were shown in our laboratory to be stable for 7 days at 4° C. After pouring and mixing the QC material from 6 different types of blood collection tube, serum immunoassay analyte levels were measured in random order on an Immulite™ 1000 analyzer (Siemens Healthcare Global, Malvern, Pa.), according to the manufacturer's instructions. $TT_3$, $TT_4$ and cortisol levels were measured by competitive immunoassays using limited immobilized antibodies and labeled hormones. During the study, one reagent lot and one calibrator lot were used for the Immulite™ 1000 analyzer.

For patient samples, blood from 5 volunteers were collected via a syringe and slowly dripped into 5 different blood collection tubes. The blood collection tubes were inverted eight times after the blood was drawn to ensure proper mixing of the blood with tube additives. Serum samples from the tubes were obtained after clotting for 60 minutes at room temperature followed by centrifugation at 1,300 g for 10 minutes. Following centrifugation, all tubes were inspected visually for complete barrier formation (except those without separator gels: glass, PRT, and ChemoPET tubes), fibrin, and hemolysis. All serum samples were processed within two hours of blood collection. The samples were then analyzed in triplicates per patient using the same protocol described above for the QC materials. One-way analysis of variance (ANOVA) and the Bonferroni correction were used to determine statistically significant differences in obtained analyte concentrations.

To determine whether chemistry analytes concentrations in ChemoPET tubes were significantly different than commercially available blood collection tubes (BD glass, RST, PRT, SST™; Greiner Vacuette™), QC or serum samples from apparently healthy volunteers were poured or collected into the different BCT types and a comprehensive metabolic panel was run from an aliquot of each tube using a Siemens Dimension RxL™ analyzer. The QC material and serum from apparently healthy volunteers were analyzed singly in random order and in the same analytical run. The analyte concentrations were not significantly or clinically different among the tube types examined.

Results and Discussion

Figure 4A:
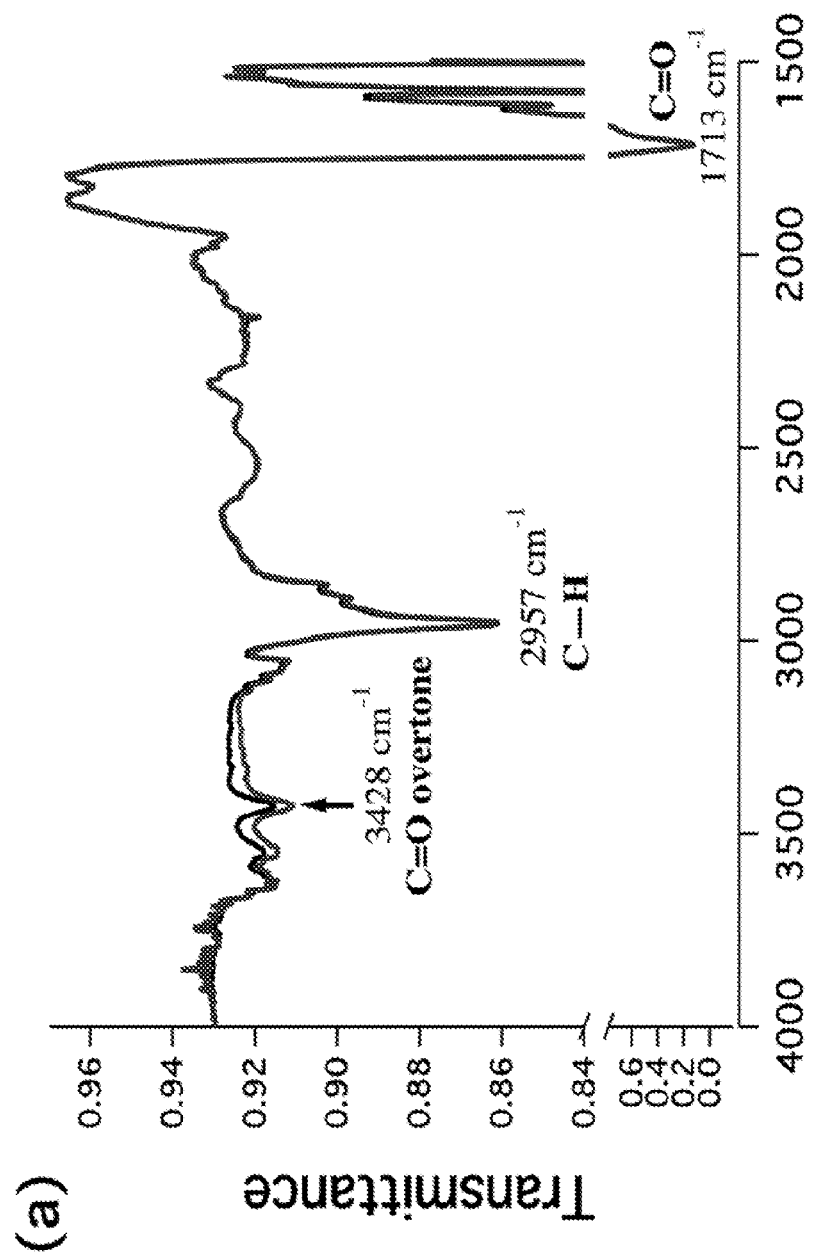
FIGS. 4a-b depict FT-IR spectra of polyethylene terephthalate modified according to the subject methods in certain embodiments.
Figure 4B:
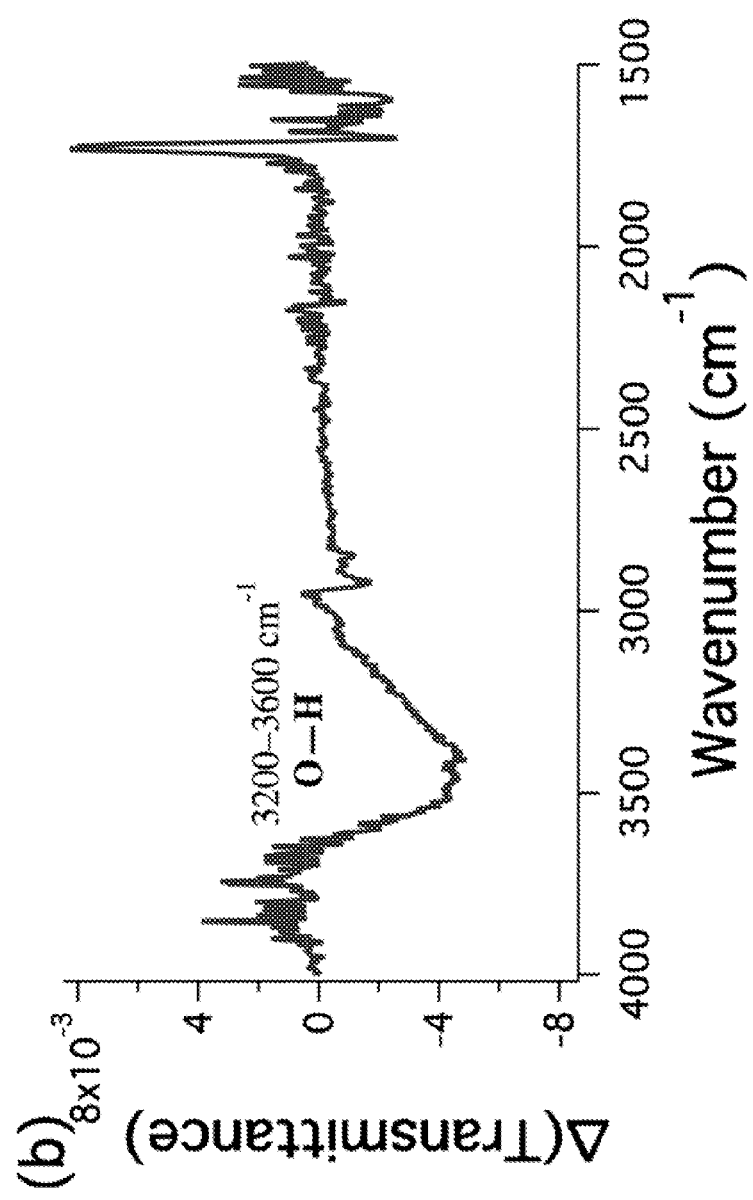
Figure 5A:
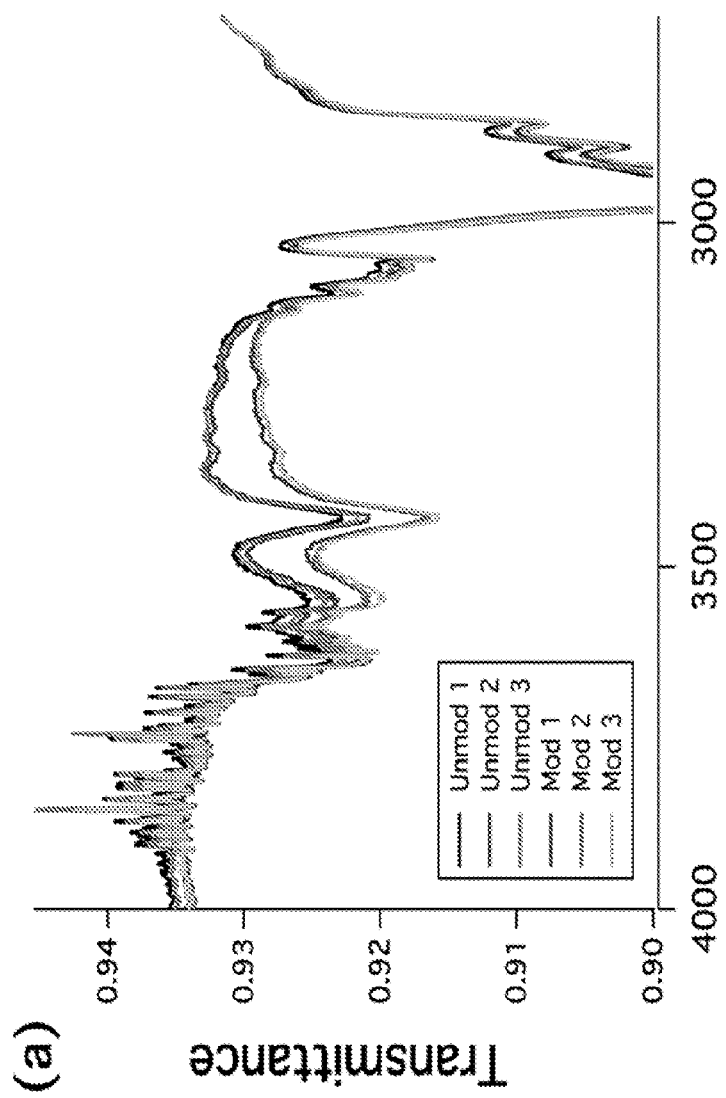
FIGS. 5a-b depict FT-IR spectra of polyethylene terephthalate modified according to the subject methods in certain embodiments.
Figure 5B:
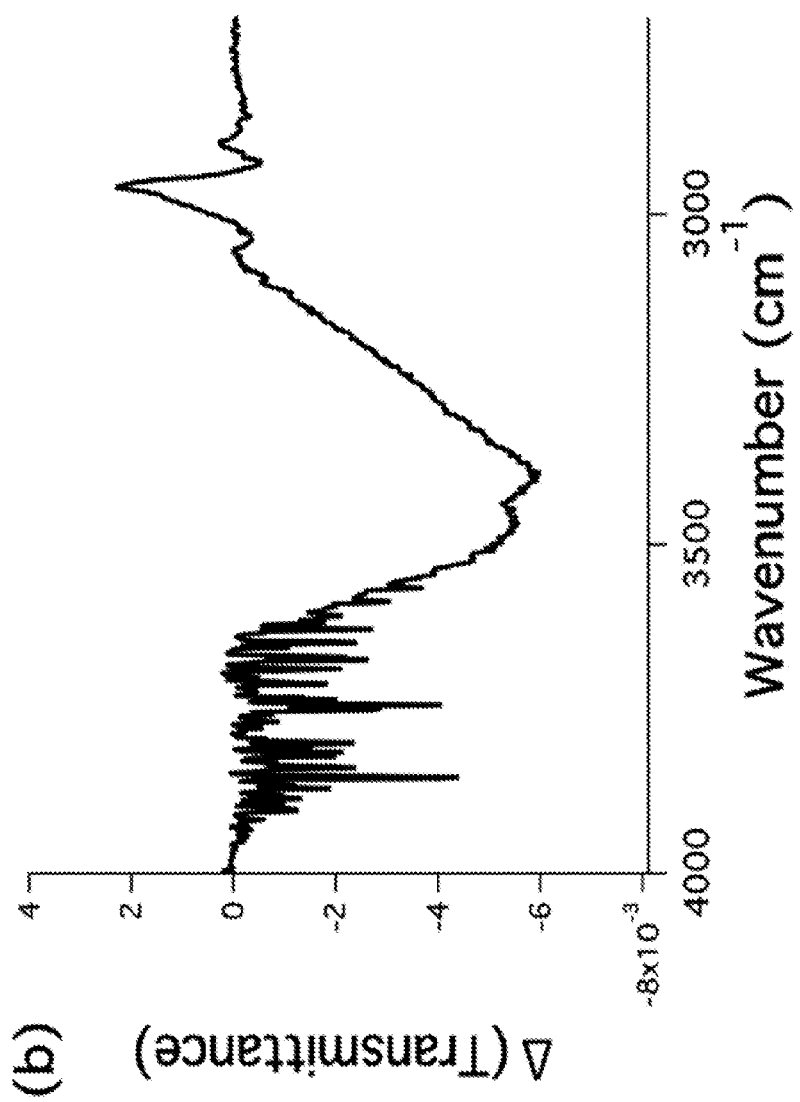

To detect the changes of functional groups at the plastic surface, FT-IR spectra of PET before and after modification were obtained. The two spectra were almost identical except in the region of 3100-3700 $cm^{-1}$ (FIG. 4A). The calculated difference spectrum revealed that the change of IR absorption in this region corresponds to the vibrational frequency of an alcoholic or phenolic O—H stretch with its typical broad peak shape (FIG. 2b). Because the modification occurs only at the top surface of the plastic and the penetration depth of the ATR mode is about 1 μm, the IR signals from added hydroxyl groups are expected to be weak. Multiple measurements at higher resolution confirmed that this difference is reproducible and larger than the noise level of the FT-IR equipment used for data acquisition (FIGS. 5A-5B).

Figure 6:
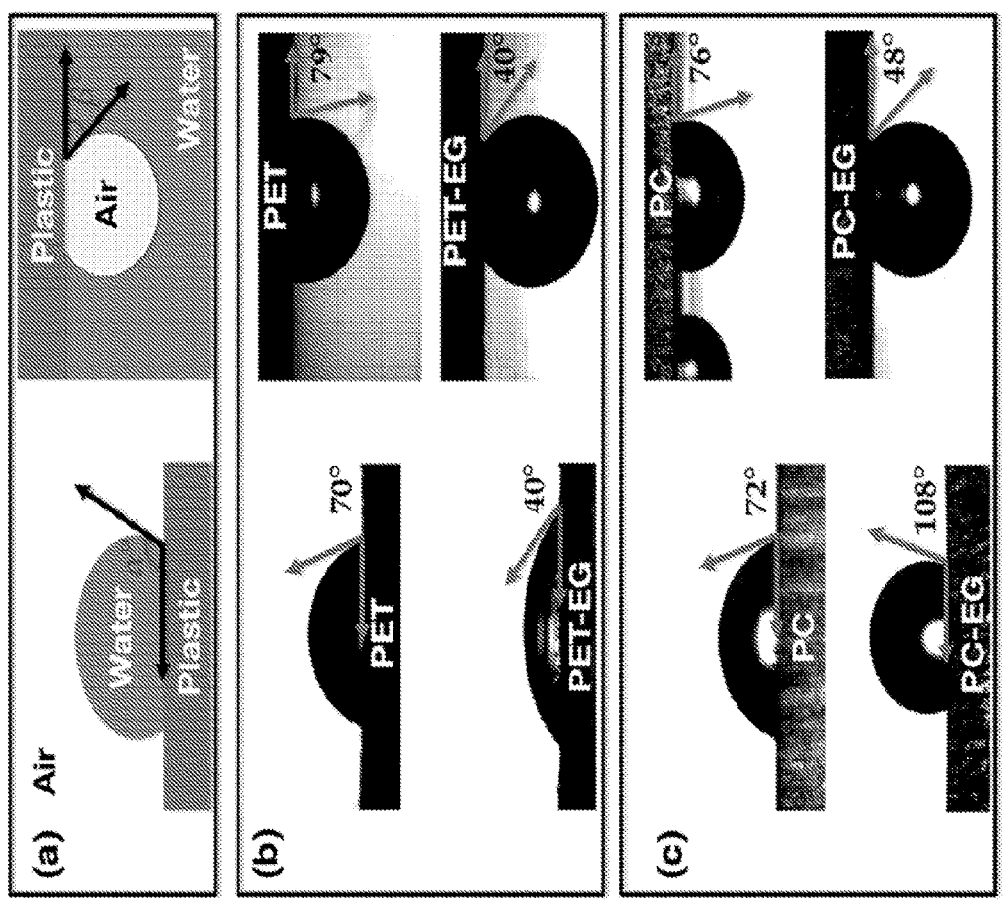
FIGS. 6a-c depict contact angle measurements on polymer surfaces modified according to the subject methods in certain embodiments.

To assess the degree of surface modification quantitatively, contact angles of water droplets were measured on the modified plastic surfaces. Successful hydrophilic transformation is indicated by the decrease of contact angles as shown in FIGS. 6A-6C.

Table 4 summarizes the contact angle data. In the case of PET, the EG-modified surface had a mean contact angle of 41±4° and was significantly smaller than the bare PET surface of 70±2°, t(7)=14.95, p<0.0001. Similarly, the GL-modified PET had an average contact angle of 58±5°, indicating that trans-esterification resulted in a significant increase in wettability, t(6)=5.20, p=0.002. But the change was not as large as EG, indicating EG has a higher reactivity than GL under the same reaction conditions (20% (v/v) TMG catalyst, 2 h reaction at room temperature). PETG, a variant of PET with an additional monomeric unit of 1,4-cyclohexanedimethanol (CHDM), showed the same trend as PET albeit with a slight difference in the starting contact angle of the unmodified surface.

For polycarbonate (PC), the room temperature reaction did not alter contact angle values much. Interestingly, when the reaction temperature was increased to 60° C., the modified plastic exhibited an even more hydrophobic surface with contact angles of 108° and 93° for EG and GL modifications, respectively, compared to 71° of the native PC surface (FIG. 6C). However, during the washing step, the water-liking nature of the modified plastic was evident in that water tended to stay on top of the modified sides of the plastic pieces and avoided the bare PC surface. When the captive bubble method was used so that the PC surface was kept wet during the measurement, chemically modified PC resulted in the contact angle (44±3°) that is significantly smaller than that of the unmodified PC (77±2°, t(6)=20.00, p<0.0001). The captive bubble method, which simulates the condition of plastic containers to be used in an aqueous solution, support the transformation of PC surface property via the base-catalyzed trans-esterification chemistry.

Figure 7:
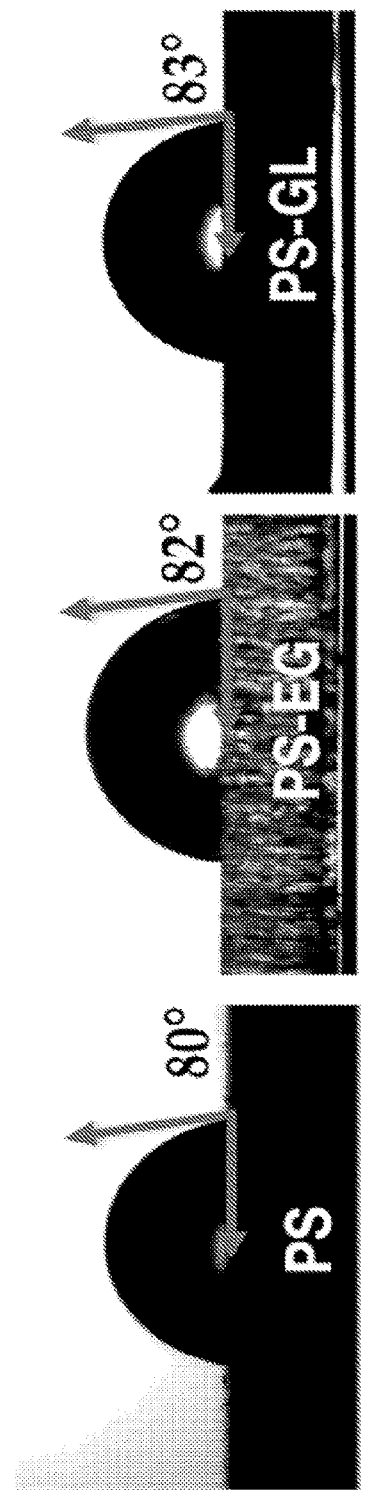
FIG. 7 depicts sessile drop contact angle measurements for polystyrene modified according to the subject methods in certain embodiments.

PS was used a control and showed little to no change of contact angle (Table 4; FIG. 7). Considering the molecular structure of polystyrene, where no reactive sites can be targeted by a nucleophilic attack, such nominal change of contact angle is an expected result.

TABLE 4

Average Contact Angles for Plastics Before and After Chemical Modification (n = 5; error is standard deviation)

| Plastics | Droplet Method Contact Angle, α (°) | Bubble Method Contact Angle, β (°) |
|---|---|---|
| PET | 70 ± 2[a] | 78 ± 2 |
| PET-EG | 41 ± 4 | 41 ± 2 |
| PET-GL | 58 ± 5 | — |
| PETG | 75 ± 1 | — |
| PETG-EG | 47 ± 1 | — |
| PETG-GL | 66 ± 4 | — |
| PC | 71 ± 3 | 77 ± 2 |
| PC-EG[b] | 108 ± 4 | 44 ± 3 |
| PC-GL[b] | 93 ± 7 | — |
| PS | 80 ± 1 | — |
| PS-EG | 82 ± 2 | — |
| PS-GL | 85 ± 3 | — |

[a]All of the reported values are averages ± standard deviations (SD, n = 5).
[b]For PC-EG: 40% (v/v) TMG in EG, 2 h incubation at 60° C. For PC-GL: 20% (v/v) TMG in GL, 2 h incubation at 60° C. All other samples: 20% (v/v) TMG in EG or GL, 2 h incubation at room temperature.

Modification of Blood Collection Tubes with Different Base Catalysts

In addition to an inorganic base, KOH, we tested two organic bases for their efficacy as catalysts for this trans-esterification of the PET surface; TBD and TMG are guanidine compounds of strong basicity (their $pK_a$ values in acetonitrile are 25.96 and 23.3, respectively), which can catalyze various types of synthetic reactions. Both TBD and TMG catalyzed the reaction to a sufficient degree of transformation into a hydrophilic surface, even at room temperature with a reaction time as short as 10 minutes. Moreover, ChemoPET tubes exhibited a lower analytical bias compared to widely adopted tube types, without the need of surfactant additives, in a number of different clinical chemistry analyses with quality control materials and blood samples from healthy volunteers.

Figure 8:
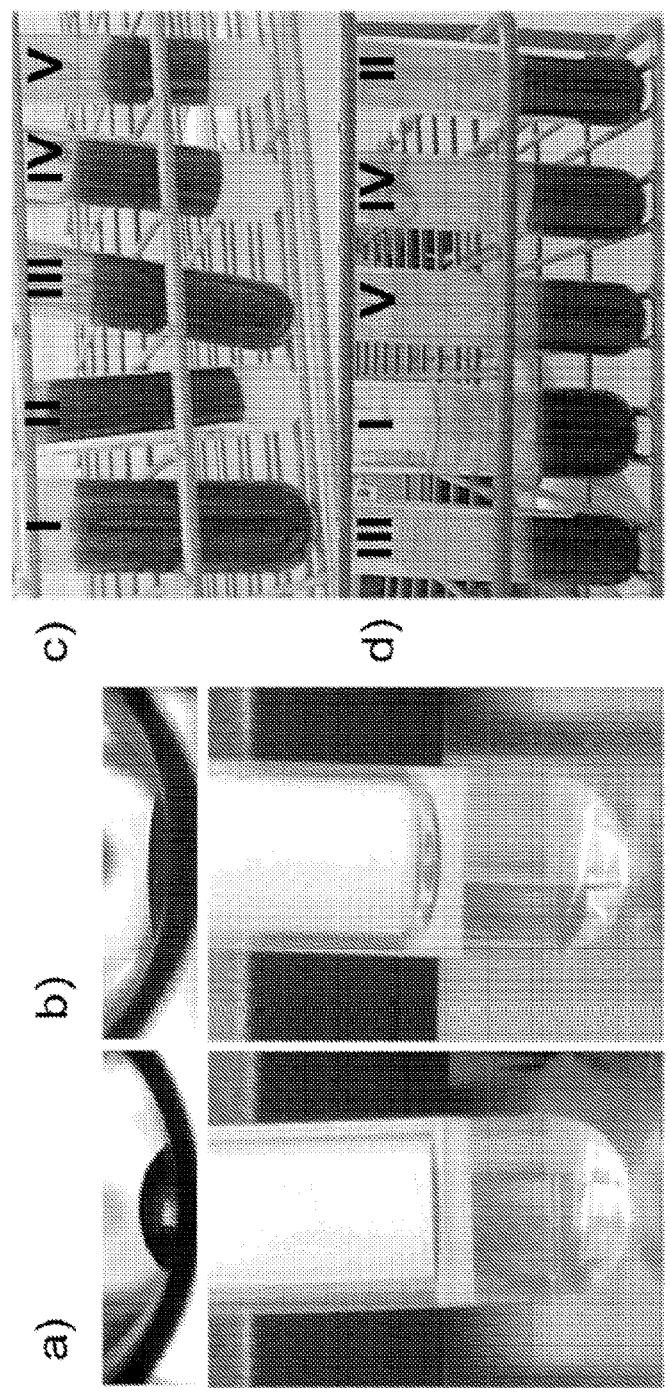
FIGS. 8a-d depict observation of contact angle and water meniscus formed inside of tubes modified by the subject methods according to certain embodiments.
Figure 9:
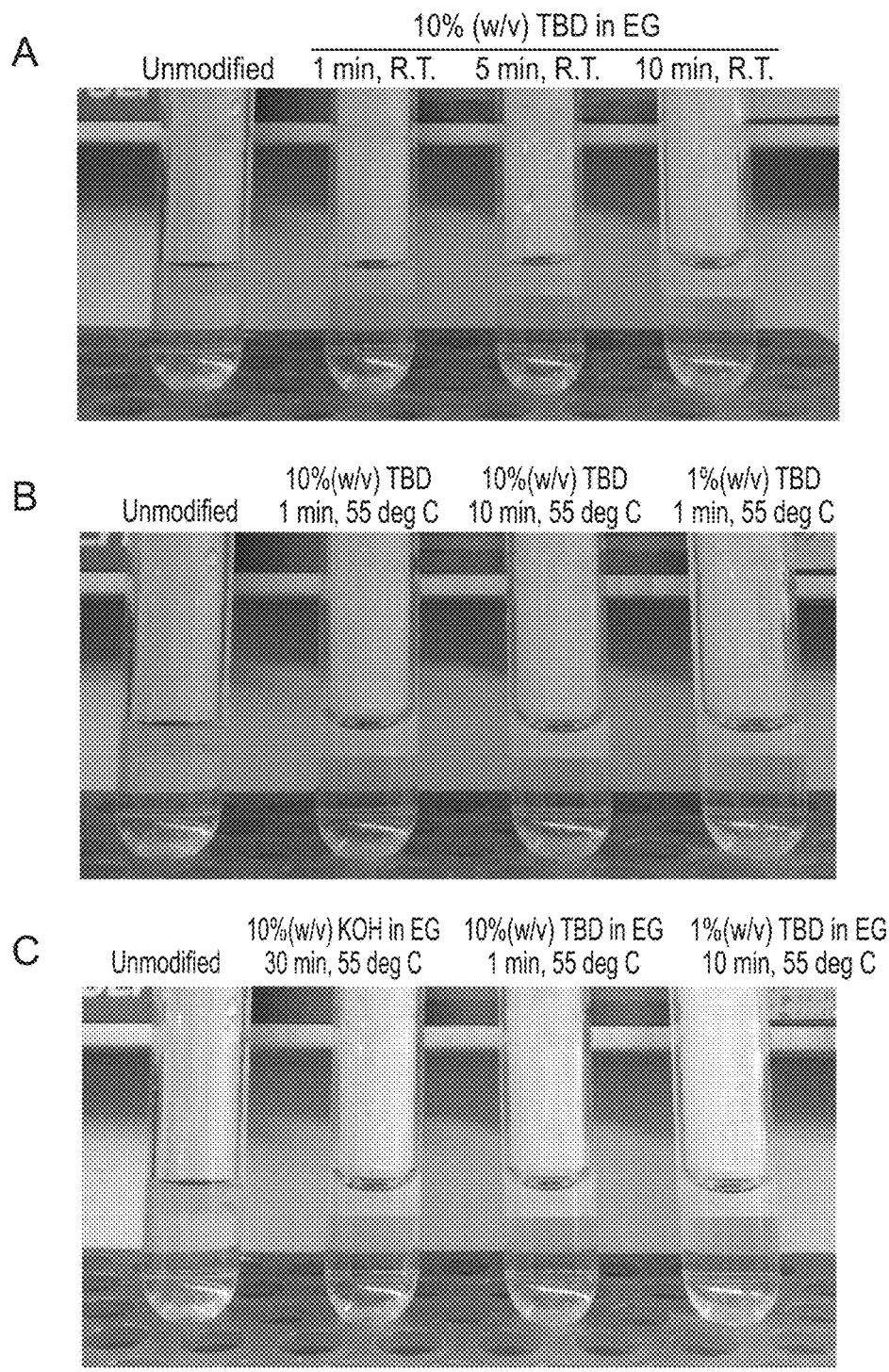
FIGS. 9a-c depict observation of water meniscus formed inside tubes modified by the subject methods according to certain embodiments.

Nonaqueous reactions with ethylene glycol in the presence of base catalysts KOH, TBD, and TMG at concentrations of 1.8, 0.72, and 1.6 M, respectively, resulted in a dramatic change of surface wettability, as observed by examining the water meniscus and contact angle (FIGS. 8A-8D and FIGS. 9A-9C). The contact angles were approximately 70° for untreated PET tubes and 30° for ChemoPET tubes (FIGS. 8A and 8B). As evident in FIG. 8B, the meniscus was nearly identical to that seen of water in glass tubes, demonstrating that the PET surface was successfully made hydrophilic. The optical transparency and the shape were unaltered by the chemical reaction. Additionally, the modified plastic tube retained its hydrophilic inner surface property and gas impermeability (i.e., holds a vacuum) for at least 12 months, as expected with the stability of covalent bonds and surface-only modification. KOH can be used to achieve a similar level of hydrophilicity as with TBD and TMG.

TABLE 5

Comparison of Cortisol, $TT_3$, and $TT_4$ Concentrations in QC Material and from Five Apparently Healthy Volunteers Processed in ChemoPET Tubes and Commercial Brands

| a) Cortisol | QC Material (n = 9) | | Healthy Volunteers (n = 5) | |
|---|---|---|---|---|
| | Conc. (μg/dL) | % Bias | Conc. (μg/dL) | % Bias |
| Glass | 42.8 ± 0.6[a] | | 8.8 ± 0.9 | |
| Modified PET | 43.6 ± 0.5 | +1.9[b] | 8.5 ± 0.9 | −3.8 |
| SST | 51.1 ± 0.7 | +19.4 | 9.3 ± 0.9 | +5.9 |
| RST | 52.8 ± 1.2 | +23.4 | 9.4 ± 1.0 | +6.1 |
| PRT | 47.1 ± 0.5 | +10.0 | — | — |
| Greiner | 45.0 ± 0.7 | +5.1 | 8.7 ± 0.9 | −1.2 |

| b) $TT_3$ | QC Material (n = 9) | | Healthy Volunteers (n = 5) | |
|---|---|---|---|---|
| | Conc. (ng/dL) | % Bias | Conc. (ng/dL) | % Bias |
| Glass | 359 ± 5 | | 83.5 ± 3.0 | |
| Modified PET | 347 ± 5 | −3.3 | 88.2 ± 3.7 | +5.7 |
| SST | 413 ± 10 | +15.0 | 97.6 ± 2.4 | +17.0 |
| RST | 406 ± 5 | +13.1 | 91.9 ± 3.9 | +10.1 |
| PRT | 379 ± 3 | +5.6 | — | — |
| Greiner | 351 ± 6 | −2.2 | 90.1 ± 2.6 | +7.9 |

| c) $TT_4$ | QC Material (n = 9) | | Healthy Volunteers (n = 5) | |
|---|---|---|---|---|
| | Conc. (μg/dL) | % Bias | Conc. (μg/dL) | % Bias |
| Glass | 15.9 ± 0.4 | | 6.1 ± 0.3 | |
| Modified PET | 15.1 ± 0.3 | −5.0 | 6.1 ± 0.3 | +0.2 |
| SST | 19.3 ± 0.4 | +21.4 | 6.9 ± 0.5 | +12.9 |
| RST | 20.1 ± 0.4 | +26.4 | 6.3 ± 0.4 | +3.5 |
| PRT | 17.2 ± 0.2 | +8.2 | — | — |
| Greiner | 15.5 ± 0.2 | −2.5 | 5.9 ± 0.3 | −2.7 |

[a]All entries are means ± standard errors.
[b]Biases are defined as deviations from values for glass.

Characterizing Performance of Prepared BCTs for Thyroid Hormone Assays

To check whether the ChemoPET tubes were compatible for blood storage and serum separation purposes, blood samples from healthy volunteers were collected into various types of BCTs and centrifuged according to tube manufacturers' recommendations. No red blood cell films on the interior wall and no hemolysis in the serum layer were observed in any of the tested tube types (FIGS. 8C and 8D). Hemolysis is the rupture of red blood cells and release of cellular constituents into serum. No difference in the mean hemolysis index of all serum samples, which was measured by a spectrophotometer, was found among the different BCT types. Additionally, the serum samples collected using ChemoPET tubes were sent to Mayo Medical Laboratories (Rochester, Minn.) for a volatile chemical screening (for methanol, ethanol, isopropanol, acetaldehyde, and acetone) and ethylene glycol quantification. The ChemoPET tubes did not contain any detectable contaminants for clinical purposes (detection limit: 10 mg/dL).

The performance of ChemoPET tubes was compared with five different types of commercially available BCTs, using two different types of samples: QC materials and blood samples from five apparently healthy volunteers. The concentrations of three analytes (cortisol, total triiodothyronine ($TT_3$), and total thyroxine ($TT_4$) were determined with an automated immunoassay instrument (Immulite™ 1000) and compared against the values obtained from glass tubes.

Glass tubes are considered the control in this study, which contain no clot activator, internal tube coating, or separator gel; therefore, any deviation of analyte concentrations from those obtained with glass tubes indicates interference caused by plastic BCTs and their additives. Table 6 summarizes the results of this experiment. No statistically significant difference is found in comparing ChemoPET tubes with glass tubes whereas this claim cannot be made for some of the other plastic tubes (see Table 6).

TABLE 6

Statistical analysis of data obtained from quality control materials: 1-way ANOVA table and confidence interval analysis using the Bonferroni correction.

(a) Cortisol
n 60

| Groups | n | Mean | SE | Pooled SE | SD |
|---|---|---|---|---|---|
| Glass | 9 | 42.84 | 0.587 | 0.741 | 1.76 |
| Greiner | 9 | 44.96 | 0.686 | 0.741 | 2.06 |
| Plain red top | 9 | 47.08 | 0.490 | 0.741 | 1.47 |
| Discard tube | 6 | 45.68 | 0.905 | 0.907 | 2.22 |
| SST | 9 | 51.11 | 0.708 | 0.741 | 2.12 |
| RST | 9 | 52.77 | 1.213 | 0.741 | 3.64 |
| mPET | 9 | 43.56 | 0.513 | 0.741 | 1.54 |

| Source of variation | Sum squares | DF | Mean square | F statistic | p |
|---|---|---|---|---|---|
| Groups | 761.24 | 6 | 126.87 | 25.70 | <0.0001 |
| Residual | 261.60 | 53 | 4.94 | | |
| Total | 1022.84 | 59 | | | |

| Bonferroni Contrast | Difference | 95% CI |
|---|---|---|
| Greiner v Glass | 2.11 | −0.76 to 4.98 |
| Plain red top v Glass | 4.23 | 1.36 to 7.10 |
| Discard tube v Glass | 2.84 | −0.37 to 6.05 |
| SST v Glass | 8.27 | 5.40 to 11.14 |
| RST v Glass | 9.92 | 7.05 to 12.79 |
| mPET v Glass | 0.71 | −2.16 to 3.58 |

(b) $TT_3$
n 60

| Groups | n | Mean | SE | Pooled SE | SD |
|---|---|---|---|---|---|
| Glass | 9 | 359.00 | 4.589 | 6.595 | 13.77 |
| Greiner | 9 | 351.33 | 5.647 | 6.595 | 16.94 |
| Plain red top | 9 | 378.56 | 3.087 | 6.595 | 9.26 |
| Discard tube | 6 | 377.00 | 13.249 | 8.078 | 32.45 |
| SST | 9 | 413.00 | 9.801 | 6.595 | 29.40 |
| RST | 9 | 406.00 | 5.326 | 6.595 | 15.98 |
| mPET | 9 | 347.11 | 5.306 | 6.595 | 15.92 |

| Source of variation | Sum squares | DF | Mean square | F statistic | p |
|---|---|---|---|---|---|
| Groups | 36073.74 | 6 | 6012.29 | 15.36 | <0.0001 |
| Residual | 20749.11 | 53 | 391.49 | | |
| Total | 56822.85 | 59 | | | |

| Bonferroni Contrast | Difference | 95% CI |
|---|---|---|
| Greiner v Glass | −7.67 | −33.23 to 17.90 |
| Plain red top v Glass | 19.56 | −6.01 to 45.12 |
| Discard tube v Glass | 18.00 | −10.58 to 46.58 |
| SST v Glass | 54.00 | 28.43 to 79.57 |
| RST v Glass | 47.00 | 21.43 to 72.57 |
| mPET v Glass | −11.89 | −37.45 to 13.68 |

TABLE 6-continued

Statistical analysis of data obtained from quality control materials: 1-way ANOVA table and confidence interval analysis using the Bonferroni correction.

(b) $TT_4$
n 60

| Groups | n | Mean | SE | Pooled SE | SD |
|---|---|---|---|---|---|
| Glass | 9 | 15.87 | 0.418 | 0.329 | 1.25 |
| Greiner | 9 | 15.53 | 0.165 | 0.329 | 0.49 |
| Plain red top | 9 | 17.24 | 0.180 | 0.329 | 0.54 |
| Discard tube | 6 | 15.63 | 0.426 | 0.403 | 1.04 |
| SST | 9 | 19.31 | 0.363 | 0.329 | 1.09 |
| RST | 9 | 20.14 | 0.448 | 0.329 | 1.34 |
| mPET | 9 | 15.11 | 0.272 | 0.329 | 0.82 |

| Source of variation | Sum squares | DF | Mean square | F statistic | p |
|---|---|---|---|---|---|
| Groups | 211.71 | 6 | 35.29 | 36.26 | <0.0001 |
| Residual | 51.58 | 53 | 0.97 | | |
| Total | 263.29 | 59 | | | |

| Bonferroni Contrast | Difference | 95% CI |
|---|---|---|
| Greiner v Glass | −0.33 | −1.61 to 0.94 |
| Plain red top v Glass | 1.38 | 0.10 to 2.65 |
| Discard tube v Glass | −0.23 | −1.66 to 1.19 |
| SST v Glass | 3.44 | 2.17 to 4.72 |
| RST v Glass | 4.28 | 3.00 to 5.55 |
| mPET v Glass | −0.76 | −2.03 to 0.52 |

For QC materials, ChemoPET and Greiner tubes showed significantly lower relative biases (+1.9% and +5.1% for cortisol; −3.3% and −2.2% for $TT_3$; −5.0% and −2.5% for $TT_4$, respectively) than BD SST, RST, and PRT tubes (e.g., for SST, +19.4% for cortisol; +15.0% for $TT_3$; +21.4% for $TT_4$, respectively; p<0.0001 from the F-test).

The positive bias values observed from PET tubes were larger than desirable bias derived from biological variations: 10.26% for cortisol, 3.53% for $TT_3$, and 3.0% for $TT_4$. For the ChemoPET tubes, the bias of 5.0% slightly exceeded the desirable bias for $TT_4$ (Table 2). For blood samples from apparently healthy volunteers, the ChemoPET and Greiner tubes again showed lower relative biases (−3.8% and −1.2% for cortisol; +5.7% and +7.9% for $TT_3$; +0.2% and −2.7% for $TT_4$, respectively) than the PET tubes (e.g., for SST, +5.9% for cortisol; +17.0% for $TT_3$; +12.9% for $TT_4$, respectively).

As shown above, nonaqueous trans-esterification with polyols catalyzed by organic bases is an efficient and inexpensive method to prepare glass-like surfaces for plastics having electrophilic backbone linkages. The scheme is effective for both PET and PC. Contact angle measurements show that the chemically modified PET and PC have been transformed from hydrophobic to hydrophilic in the presence of water. The chemically modified plastics are found to retain their optical and mechanical properties and the modification is permanent and does not leach residue. Emphasis was placed on comparing chemically modified PET blood collection tubes with commercial PET tubes that have been treated by the manufacturers with surfactant coatings. Test results for the standard analysis of $TT_3$, $TT_4$ and cortisol in blood showed that the modified tubes have little to no detrimental effect to assays and tests for which the collected blood is used. The tubes perform similarly to glass blood collection tubes, which are considered to be the gold standard in blood analyses but cannot be used in hospitals because of the risk of cuts from broken glass containers exposed to blood. In consideration of cost and catalytic activity (Table 7),

TABLE 7

Reaction conditions and material costs of reagents

| Compound | Concentration | Temperature/ Duration | Cost (Sigma) |
|---|---|---|---|
| KOH | 10% (w/v) = 1.8M | 55° C., 30 min | 99.99% purity $313.00/500 g = $35/mol 90% purity $218.50/10 kg = $1.2/mol |
| TBD | 10% (w/v) = 0.72M 1% (w/v) = 0.072M | 22° C., 10 min 55° C., 1 min 55° C., 1 min | 98% purity $57.80/5 g = $1609/mol |
| TMG | 20% (v/v) = 1.6M 40% (v/v) = 3.2M | 22° C., 10-120 min 60° C., 120 min | 99% purity $176.00/500 mL = $44/mol |
| EG | n/a | n/a | 99.8% purity (anhydrous) $403.50/6 L = $3.75/mol |

The catalysts are not consumed but recycled; and the amount of ethylene glycol reactant used is also minimal per reaction because only the surface layer is modified. Good uniformity and stability of surface modification was observed. This above results demonstrate that the interior surface of polyester and polycarbonate blood collection tubes prepared according to the subject methods can render polyester and polycarbonate surfaces to have glass-like properties on the inside of a container. The test results for immunoassays using QC materials and patient blood samples demonstrated excellent performance of surface modified tubes as compared to those tested above. These results also demonstrate that there was no leaching of the surface modification from the polymer substrate prepared by the subject methods.

Example 3

PET Blood Collection Tubes Used

The following types of evacuated blood collection tubes were examined: (1) a plastic Vacuette™ (Greiner Bio-One™, gold-top tube with gel separator; 13×75 mm, cat. no. 454228; lot B091209, Monroe, N.C.); (2) a glass tube (Becton Dickinson (BD, Franklin Lakes, N.J.); red-top Vacutainer™ no-additive blood tube; 16×100 mm, cat. no. 366441; lot 2219385 from BD); (3) a plastic SST™ tube (BD, gold-top Vacutainer™ tube with gel separator; 13×75 mm, cat. no. 367983; lot 2258708); (4) a plastic RST™ tube (BD, orange-top Vacutainer™ tube with gel separator; 13×100 mm, cat. no. 368774; lot 120804); (5) a plastic plain red-top (PRT) tube (BD, Vacutainer™ tube with no gel separator; 13×100 mm, cat. no. 367814; lot 2200653); and (6) a chemically modified tubes were made from unmodified PET tubes (BD, 3-mL Vacutainer™ tubes with no interior coating; 3 mL, cat. no. 366703; lot 2160209). Glass tubes are used as controls. The glass tubes contain no clot activator, internal tube coating, or separator gel.

For patient samples, blood from 50 apparently healthy volunteers were collected via a syringe and slowly dripped into 7 different blood collection tubes. The blood collection tubes were inverted eight times after the blood was drawn to ensure proper mixing of the blood with tube additives. Serum samples from the tubes were obtained after clotting for 60 minutes at room temperature followed by centrifugation at 1,300 g for 10 minutes. Following centrifugation, all tubes were inspected visually for complete barrier formation (except those without separator gels: glass, PRT, and ChemoPET tubes), fibrin, and hemolysis. All serum samples were processed within two hours of blood collection. The samples were then analyzed in triplicates per patient using the same protocol described for the QC materials. One-way analysis of variance (ANOVA) and the Bonferroni correction were used to determine statistically significant differences in obtained analyte concentrations.

TABLE 8

(a) Cortisol

| | Apparently Healthy Volunteers blood (n = 50) | |
|---|---|---|
| Tube Types | Mean ± S.E. (μg/dL) | Bias (from glass tube) |
| Glass | 9.5 ± 0.3 | |
| Surface-Modified Polyethylene Terephthalate according to the Subject Methods | 9.9 ± 0.4 | +4.2% |
| Serum Separator Tube (SST) | 9.7 ± 0.4 | −2.1% |
| Rapid Serum Tube (RST) | 9.8 ± 0.4 | +3.2% |
| Plain | 9.4 ± 0.3 | −1.1% |
| Greiner Vacuette PET tube | 9.6 ± 0.3 | +1.1% |
| Unmodified Polyethylene Terephthalate | 9.4 ± 0.3 | −1.1% |

The results in Table 8a showed no significant differences in cortisol concentrations among tube types (F=0.35; p=0.912). The cortisol desirable bias based on biological variation is +/−10.26%. The data also demonstrates that no clinically significant difference in cortisol concentrations among tube types (Compared to glass tubes, biases among tube type were not above or below 10.26%)

(b) $TT_3$ (total triiodothyronine)

| | Apparently Healthy Volunteers blood (n = 50) | |
|---|---|---|
| Tube Types | Mean ± S.E. (μg/dL) | Bias (from glass tube) |
| Glass | 90.3 ± 1.4 | |
| Surface-Modified Polyethylene Terephthalate according to the Subject Methods | 92.9 ± 2.9 | +2.9% |
| Serum Separator Tube (SST) | 91.4 ± 1.6 | +1.2% |
| Rapid Serum Tube (RST) | 89.5 ± 1.3 | −0.9% |
| Plain | 90.6 ± 1.4 | +0.3% |
| Greiner Vacuette PET tube | 92.1 ± 3.9 | +2.0% |
| Unmodified Polyethylene Terephthalate | 91.9 ± 1.5 | +1.8% |

The results in Table 8b showed no significant differences in total triiodothyronine concentrations among tube types were observed (F=0.35; p=0.909). The triiodothyronine desirable bias based on biological variation is +/−3.53%. The data also demonstrates that no clinically significant difference in total triiodothyronine concentrations among tube types (Compared to glass tubes, biases among tube type were not above or below 3.53%)

(c) TT$_4$ (total thyroxine)

| Tube Types | Apparently Healthy Volunteers blood (n = 50) | |
|---|---|---|
| | Mean ± S.E. (µg/dL) | Bias (from glass tube) |
| Glass | 7.0 ± 0.1 | |
| Surface-Modified Polyethylene Terephthalate according to the Subject Methods | 7.1 ± 0.1 | +1.4% |
| Serum Separator Tube (SST) | 7.2 ± 0.1 | +2.9% |
| Rapid Serum Tube (RST) | 7.0 ± 0.1 | 0.0% |
| Plain | 7.0 ± 0.1 | 0.0% |
| Greiner Vacuette PET tube | 6.9 ± 0.1 | −1.4% |
| Unmodified Polyethylene Terephthalate' | 7.0 ± 0.1 | 0.0% |

The results in Table 8c showed no significant differences in total thyroxine concentrations among tube types were observed (F=0.45; p=0.847). The thyroxine desirable bias based on biological variation is +/−3.0%. The data also demonstrates that no clinically significant difference in total thyroxine concentrations among tube types (Compared to glass tubes, biases among tube type were not above or below 3.0%)

Example 4

For QC materials, a polyester (e.g., PET) test tube which has been modified in accordance with the subject methods and Greiner Vacuette tubes show significantly lower relative biases (−9.2% and −10.8% for cortisol; −0.6% and +0.6% for TT$_3$; +2.5% and +7.5% for TT$_4$, respectively) than BD tubes (e.g., for SST, −4.6% for cortisol; +10.1% for TT$_3$; +10.0% for TT$_4$, respectively). The positive bias values observed for most BD tubes for TT$_3$ and TT$_4$, are larger than desirable bias values based on biological variation: 10.26%, 3.53%, and 3.00% for cortisol, TT$_3$, and TT$_4$, respectively. Thus, a polyester (e.g., PET) test tube, which has been modified in accordance with the subject methods tubes show much less biases than BD tubes.

TABLE 8

Comparison of immunoassay test results from polyester test tubes modified in accordance with the subject methods (e.g., surface modified polyethylene terephthalate) and examples of commercially available test tubes (a) Cortisol

| | QC material (n =10) | |
|---|---|---|
| | Mean ± S.E. (µg/dL) | Bias |
| Glass | 6.5 ± 0.1 | |
| Surface-Modified Polyethylene Terephthalate according to the Subject Methods | 5.9 ± 0.1 | −9.2% |
| Serum Separator Tube (SST) | 6.2 ± 0.1 | −4.6% |
| Rapid Serum Tube (RST) | 6.6 ± 0.1 | +1.5% |
| Plain | 6.1 ± 0.1 | −6.2% |
| Greiner Vacuette PET tube | 5.8 ± 0.0 | −10.8% |

TABLE 8-continued

Comparison of immunoassay test results from polyester test tubes modified in accordance with the subject methods (e.g., surface modified polyethylene terephthalate) and examples of commercially available test tubes (b) TT$_3$ (total triiodothyronine)

| | QC material (n = 10) | |
|---|---|---|
| | Mean ± S.E. (ng/dL) | Bias |
| Glass | 80.0 ± 1.5 | |
| Surface-Modified Polyethylene Terephthalate according to the Subject Methods | 79.5 ± 1.0 | −0.6% |
| Serum Separator Tube (SST) | 88.1 ± 1.4 | +10.1% |
| Rapid Serum Tube (RST) | 83.5 ± 1.5 | +4.8% |
| Plain | 84.9 ± 1.0 | +6.1% |
| Greiner Vacuette PET tube | 80.5 ± 1.1 | +0.6% |

(c) TT$_4$ (thyroxine)

| | QC material (n = 10) | |
|---|---|---|
| | Mean ± S.E. (µg/dL) | Bias |
| Glass | 4.0 ± 0.0 | |
| Surface-Modified Polyethylene Terephthalate according to the Subject Methods | 4.1 ± 0.0 | +2.5% |
| Serum Separator Tube (SST) | 4.4 ± 0.0 | +10.0% |
| Rapid Serum Tube (RST) | 4.2 ± 0.0 | +5.0% |
| Plain | 4.4 ± 0.0 | +10.0% |
| Greiner Vacuette PET tube | 4.3 ± 0.0 | +7.5% |

Example 5

As shown below in Table 9a no significant differences were shown in cortisol concentrations among tube types were observed (F=0.35; p=0.912). The cortisol desirable bias based on biological variation is +/−10.26%. The data also demonstrates that no clinically significant difference in cortisol concentrations among tube types (Compared to glass tubes, biases among tube type were not above or below 10.26%)

TABLE 9

(a) Cortisol

| Tube Types | QC material (n = 3) | |
|---|---|---|
| | Mean ± S.E. (µg/dL) | Bias (from glass tube) |
| Glass | 24.6 ± 0.5 | |
| Surface-Modified Polyethylene Terephthalate according to the Subject Methods | 25.0 ± 0.4 | +1.6% |
| Serum Separator Tube (SST) | 25.7 ± 0.4 | +4.5% |
| Rapid Serum Tube (RST) | 26.0 ± 0.5 | +5.7% |
| Plain | 25.1 ± 0.4 | +2.0% |
| Greiner Vacuette PET tube | 25.7 ± 0.4 | +4.5% |
| Unmodified Polyethylene Terephthalate | 25.1 ± 0.3 | +2.0% |

As shown below in Table 9b no significant differences in total triiodothyronine concentrations among tube types were observed (F=0.35; p=0.909). The triiodothyronine desirable bias based on biological variation is +/−3.53%. The data also demonstrates that no clinically significant difference in total triiodothyronine concentrations among tube types (Compared to glass tubes, biases among tube type were not above or below 3.53%)

(b) $TT_3$ (total triiodothyronine)

| Tube Types | QC material (n = 3) | |
|---|---|---|
| | Mean ± S.E. (µg/dL) | Bias (from glass tube) |
| Glass | 167.8 ± 4.1 | |
| Surface-Modified Polyethylene Terephthalate according to the Subject Methods | 166.7 ± 2.9 | −0.7% |
| Serum Separator Tube (SST) | 174.8 ± 4.0 | +4.2% |
| Rapid Serum Tube (RST) | 176.0 ± 4.2 | +4.9% |
| Plain | 178.3 ± 3.3 | +6.3% |
| Greiner Vacuette PET tube | 176.7 ± 5.4 | +5.3% |
| Unmodified Polyethylene Terephthalate | 175.4 ± 2.3 | +4.5% |

As shown below in Table 9c no significant differences in total thyroxine concentrations among tube types were observed (F=0.45; p=0.847). The thyroxine desirable bias based on biological variation is +/−3.00%. The data also demonstrates that no clinically significant difference in total thyroxine concentrations among tube types (Compared to glass tubes, biases among tube type were not above or below 3.00%)

(c) $TT_4$ (total thyroxine)

| Tube Types | QC material (n = 3) | |
|---|---|---|
| | Mean ± S.E. (µg/dL) | Bias (from glass tube) |
| Glass | 9.1 ± 0.1 | |
| Surface-Modified Polyethylene Terephthalate according to the Subject Methods | 9.4 ± 0.1 | +3.3% |
| Serum Separator Tube (SST) | 9.1 ± 0.1 | 0.0% |
| Rapid Serum Tube (RST) | 9.3 ± 0.1 | +2.2% |
| Plain | 9.5 ± 0.2 | +4.4% |
| Greiner Vacuette PET tube | 9.6 ± 0.2 | +5.5% |
| Unmodified Polyethylene Terephthalate | 9.4 ± 0.1 | +3.3% |

Notwithstanding the appended clauses, the disclosure set forth herein is also defined by the following clauses:

1. A method of modifying a surface of a non-porous hydrophobic polymer substrate, the method comprising:
   contacting the surface of the non-porous hydrophobic polymer substrate with a liquid composition comprising a nucleophilic reagent and a catalyst, wherein the non-porous hydrophobic polymer substrate comprises a polymer having a backbone containing electrophilic linkages; and
   maintaining the composition in contact with the surface of the hydrophobic polymer substrate in a manner sufficient to convert at least a portion of the surface from hydrophobic to hydrophillic by transesterification while retaining the mechanical and optical properties of the polymer substrate.
2. The method according to clause 1, wherein maintaining comprises maintaining the composition in contact with the polymer substrate at a temperature that is 10° C. or more below the glass transition temperature of the polymer.
3. The method according to clause 1, wherein maintaining comprises maintaining the composition in contact with the polymer substrate at room temperature.
4. The method according to clause 1, wherein maintaining comprises maintaining the composition in contact with the polymer substrate for 30 minutes or less.
5. The method according to clause 4, wherein maintaining comprises maintaining the composition in contact with the polymer substrate for 10 minutes or less.
6. The method according to clause 1, wherein the polymer substrate is polyester.
7. The method according to clause 6, wherein the polyester is polyethylene terephthalate or derivatives thereof.
8. The method according to clause 1, wherein the nucleophilic reagent is a polyol.
9. The method according to clause 8, wherein the polyol is ethylene glycol or glycerol.
10. The method according to clause 1, wherein the catalyst is a base.
11. The method according to clause 10, wherein the base is a guanidine-containing compound or a hydroxide.
12. The method according to clause 11, wherein the guanidine-containing compound is 1,1,3,3-tetramethylguanidine.
13. The method according to clause 1, wherein the composition is non-aqueous.
14. The method according to clause 1, wherein the method comprises decreasing the contact angle made by water with the surface of the polymer substrate.
15. The method according to clause 1, wherein the hydrophobic polymer substrate is selected from the group consisting of a culture dish, blood collection tube, test tube, centrifuge tube, culture tube, microtube, syringe, fluidic conduit, medical tubing, cap, pipette, microtiter plate, flask, beaker, straw, catheter, cuvette, polymeric lens, jar, can, cup, bottle, rectilinear polymeric container, food storage container, intravenous drug delivery bag and blood transfusion bag.
16. The method according to clause 1, wherein the hydrophobic polymer substrate is a surface of a container.
17. The method according to clause 16, wherein maintaining comprises converting an interior surface of the container from hydrophobic to hydrophillic, while retaining the exterior surface of the container as hydrophobic.
18. The method according to clause 16, wherein the transparency of the polymer container does not change.
19. The method according to clause 16, wherein the shape of the polymer container does not change.
20. The method according to clause 16, wherein the polymer container is a test tube comprising polyethylene terephthalate or derivatives thereof.
21. A method of modifying an interior surface of a polymer container, the method comprising:
   contacting an interior surface of a polymer container with a composition comprising a nucleophilic reagent and a catalyst, wherein the polymer container comprises a polymer having a backbone containing electrophilic linkages; and
   maintaining the composition in contact with the interior surface of the polymer container in a manner sufficient to convert at least a portion of the surface from hydrophobic to hydrophilic by transesterification while retaining the mechanical and optical properties of the polymer container.
22. The method according to clause 21, wherein the method comprises decreasing the contact angle made by water with the polymer container surface.
23. The method according to clause 22, wherein the contact angle made by water with the polymer container surface is decreased by 10° or more.

24. The method according to clause 21, wherein maintaining comprises maintaining the composition in contact with the interior surface of the polymer container at a temperature that is 10° C. or more below the glass transition temperature of the polymer.

25. The method according to clause 21, wherein maintaining comprises maintaining the composition in contact with the interior surface of the polymer container at room temperature.

26. The method according to clause 21, wherein maintaining comprises maintaining the composition in contact with the interior surface of the polymer container for 30 minutes or less.

27. The method according to clause 26, wherein maintaining comprises maintaining the composition in contact with the interior surface of the polymer container for 10 minutes or less.

28. The method according to clause 21, wherein the method further comprises washing the modified surface.

30. The method according to clause 21, wherein the polymer container is a polyethylene terephthalate container.

31. The method according to clause 21, wherein the nucleophilic reagent is a polyol.

32. The method according to clause 31, wherein the polyol is ethylene glycol.

33. The method according to clause 21, wherein the catalyst is a base.

34. The method according to clause 33, wherein the base is a guanidine-containing compound.

35. The method according to clause 34, wherein the guanidine-containing compound is 1,1,3,3-tetramethylguanidine.

36. The method according to clause 35, wherein the base is potassium hydroxide.

37. The method according to clause 21, wherein the composition is non-aqueous.

38. The method according to clause 21, wherein the composition does not include a solvent.

39. The method according to clause 21, wherein the composition consists of a nucleophilic agent and a catalyst.

40. The method according to clause 39, wherein the composition consists of ethylene glycol and a catalytic amount of 1,1,3,3-tetramethylguanidine.

41. The method according to clause 39, wherein the composition consists of ethylene glycol and a catalytic amount of potassium hydroxide.

42. The method according to clause 21, wherein the polymer container is selected from the group consisting of blood collection tube, test tube, centrifuge tube, culture tube, microtube, syringe, fluidic conduit, medical tubing, cap, pipette, microtiter plate, flask, beaker, straw, catheter, cuvette, jar, can, cup, bottle, rectilinear polymeric container, food storage container, intravenous drug delivery bag and blood transfusion bag.

43. The method according to clause 42, wherein the polymer container comprises a hydrophobic interior surface and a hydrophobic exterior surface.

44. The method according to clause 43, wherein maintaining comprises converting the interior surface from hydrophobic to hydrophillic, while retaining the exterior surface as hydrophobic.

45. The method according to clause 21, wherein the transparency of the polymer container does not change.

46. The method according to clause 21, wherein the shape of the polymer container does not change.

47. A polymer container comprising a transesterified hydrophillic interior surface.

48. The polymer container according to clause 47, wherein the polymer container comprises a hydrophobic exterior surface.

49. The polymer container according to clause 47, wherein the polymer container comprises a backbone containing electrophilic linkages.

50. The polymer containiner according to clause 47, wherein the polymer container comprises polyethylene terephthalate and the hydrophilic interior surface of the container comprises transesterified polyethylene terephthalate.

51. The polymer container according to clause 47, wherein the container is configured to hold a volume of liquid from 0.001 mL to 1000 mL.

52. The polymer container according to clause 47, wherein the container is selected from the group consisting of a blood collection tube, test tube, centrifuge tube, culture tube, microtube, syringe, fluidic conduit, medical tubing, cap, pipette, microtiter plate, flask, beaker, straw, catheter, cuvette, jar, can, cup, bottle, rectilinear polymeric container, food storage container, intravenous drug delivery bag and blood transfusion bag.

53. The polymer container according to clause 47, wherein the polymer container is configured to provide a contact angle of water on the interior surface of the polymer container of 60° or less.

54. The polymer container according to clause 53, wherein the polymer container is configured to provide a contact angle of water on the interior surface of the polymer container of 30° or less.

55. The polymer container according to clause 47, wherein the polymer container is transparent.

56. The polymer container according to clause 47, wherein the polymer container has substantially the same mechanical and optical properties as a polymer container having an unmodified hydrophobic interior surface.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of modifying a surface of a non-porous hydrophobic polymer substrate, the method comprising:
   contacting the surface of the non-porous hydrophobic polymer substrate with a liquid composition comprising a nucleophilic reagent and a catalyst, wherein the non-porous hydrophobic polymer substrate comprises a polymer having a backbone containing electrophilic linkages; and
   maintaining the composition in contact with the surface of the hydrophobic polymer substrate in a manner sufficient to convert at least a portion of the surface from hydrophobic to hydrophilic by transesterification while retaining the mechanical and optical properties of the polymer substrate.

2. The method according to claim 1, wherein maintaining comprises maintaining the composition in contact with the polymer substrate at a temperature that is 10° C. or more below the glass transition temperature of the polymer.

3. The method according to claim 1, wherein maintaining comprises maintaining the composition in contact with the polymer substrate at room temperature.

4. The method according to claim 1, wherein the polymer substrate is polyester or polycarbonate.

5. The method according to claim 1, wherein the nucleophilic reagent is a polyol selected from ethylene glycol and glycerol.

6. The method according to claim 1, wherein the catalyst is a base selected from a guanidine-containing compound and a hydroxide.

7. The method according to claim 1, wherein the hydrophobic polymer substrate is selected from the group consisting of a culture dish, blood collection tube, test tube, centrifuge tube, culture tube, microtube, syringe, fluidic conduit, chromatography column walls, medical tubing, cap, pipette, microtiter plate, flask, beaker, straw, catheter, cuvette, polymeric lens, jar, can, cup, bottle, rectilinear polymeric container, food storage container, intravenous drug delivery bag and blood transfusion bag.

8. The method according to claim 1, wherein the hydrophobic polymer substrate is a surface of a container.

9. The method according to claim 8, wherein maintaining comprises converting an interior surface of the container from hydrophobic to hydrophilic, while retaining the exterior surface of the container as hydrophobic.

10. A method of modifying an interior surface of a polymer container, the method comprising:
    contacting an interior surface of a polymer container with a composition comprising a nucleophilic reagent and a catalyst, wherein the polymer container comprises a polymer having a backbone containing electrophilic linkages; and
    maintaining the composition in contact with the interior surface of the polymer container in a manner sufficient to convert at least a portion of the surface from hydrophobic to hydrophilic by transesterification while retaining the mechanical and optical properties of the polymer container.

11. The method according to claim 10, wherein maintaining comprises maintaining the composition in contact with the interior surface of the polymer container at a temperature that is 10° C. or more below the glass transition temperature of the polymer.

12. The method according to claim 10, wherein maintaining comprises maintaining the composition in contact with the interior surface of the polymer container at room temperature.

13. The method according to claim 10, wherein maintaining comprises maintaining the composition in contact with the interior surface of the polymer container for 30 minutes or less.

* * * * *